(12) United States Patent
Chou et al.

(10) Patent No.: US 10,106,856 B2
(45) Date of Patent: Oct. 23, 2018

(54) METHOD FOR EVALUATING THE EFFICACY OF AN EGFR-TKI TREATMENT

(71) Applicant: LIHPAO LIFE SCIENCE CORP., New Taipei (TW)

(72) Inventors: Teh-Ying Chou, Taipei (TW); Chun-Ming Tsai, Taipei (TW)

(73) Assignee: LIHPAO LIFE SCIENCE CORP., New Taipei (TW)

( * ) Notice: Subject to any disclaimer, the term of this patent is extended or adjusted under 35 U.S.C. 154(b) by 106 days.

(21) Appl. No.: 14/643,197

(22) Filed: Mar. 10, 2015

(65) Prior Publication Data

US 2015/0252435 A1 Sep. 10, 2015

Related U.S. Application Data

(60) Provisional application No. 61/950,288, filed on Mar. 10, 2014.

(51) Int. Cl.
| | | |
|---|---|---|
| *C12Q 1/68* | (2018.01) | |
| *C12P 19/34* | (2006.01) | |
| *C07H 21/04* | (2006.01) | |
| *C12Q 1/6886* | (2018.01) | |

(52) U.S. Cl.
CPC ..... *C12Q 1/6886* (2013.01); *C12Q 2600/106* (2013.01); *C12Q 2600/156* (2013.01); *C12Q 2600/158* (2013.01)

(58) Field of Classification Search
CPC ............ C12Q 2600/156; C12Q 1/6883; C12Q 1/6886
See application file for complete search history.

(56) References Cited

PUBLICATIONS

Kim, J. C. et al. Familial Cancer 3: 129-137, 2004.*
Lo Y.-L. et al. Lung Cancer 72 (2011) 280-286.*
Kim Y. M. et al. BMB Reports, 2010; 43(10): 693-697.*
Sakiyama T. et al. Int. J. Cancer: 114, 730-737 (2005) (Year: 2005).*
Raptis, S. et al. JNCI, vol. 99, Issue 6, Mar. 21, 2007, p. 463-474 (Year: 2007).*

\* cited by examiner

*Primary Examiner* — Stephen T Kapushoc
(74) *Attorney, Agent, or Firm* — Birch, Stewart, Kolasch & Birch, LLP

(57) ABSTRACT

The present invention provides a method for evaluating the efficacy of an EGFR-TKI treatment to a subject, comprising identifying the V384D mutation in said subject. By identifying said mutation, the efficacy of the EGFR-TKI treatment and the progression-free survival of said subject after treatment can be estimated.

6 Claims, 12 Drawing Sheets
Specification includes a Sequence Listing.

SEQUENCE LISTING

```
<160> NUMBER OF SEQ ID NOS: 8

<210> SEQ ID NO 1
<211> LENGTH: 756
<212> TYPE: PRT
<213> ORGANISM: Homo sapiens

<400> SEQUENCE: 1

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
                20                  25                  30

Lys Glu Met Ile Glu Asn Cys Leu Asp Ala Lys Ser Thr Ser Ile Gln
            35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
                100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
```

-continued

```
                180                 185                 190
Ser Val Lys Lys Gln Gly Glu Thr Val Ala Asp Val Arg Thr Leu Pro
            195                 200                 205
Asn Ala Ser Thr Val Asp Asn Ile Arg Ser Ile Phe Gly Asn Ala Val
            210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
            260                 265                 270
Arg Lys Ala Ile Glu Thr Val Tyr Ala Ala Tyr Leu Pro Lys Asn Thr
            275                 280                 285
His Pro Phe Leu Tyr Leu Ser Leu Glu Ile Ser Pro Gln Asn Val Asp
            290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
            340                 345                 350
Ala Gly Pro Ser Gly Glu Met Val Lys Ser Thr Thr Ser Leu Thr Ser
            355                 360                 365
Ser Ser Thr Ser Gly Ser Ser Asp Lys Val Tyr Ala His Gln Met Asp
            370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
            420                 425                 430
Glu Leu Pro Ala Pro Ala Glu Val Ala Ala Lys Asn Gln Ser Leu Glu
            435                 440                 445
Gly Asp Thr Thr Lys Gly Thr Ser Glu Met Ser Glu Lys Arg Gly Pro
            450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
            500                 505                 510
Ile Asn Glu Gln Gly His Glu Val Leu Arg Glu Met Leu His Asn His
            515                 520                 525
Ser Phe Val Gly Cys Val Asn Pro Gln Trp Ala Leu Ala Gln His Gln
            530                 535                 540
Thr Lys Leu Tyr Leu Leu Asn Thr Thr Lys Leu Ser Glu Glu Leu Phe
545                 550                 555                 560
Tyr Gln Ile Leu Ile Tyr Asp Phe Ala Asn Phe Gly Val Leu Arg Leu
                565                 570                 575
Ser Glu Pro Ala Pro Leu Phe Asp Leu Ala Met Leu Ala Leu Asp Ser
            580                 585                 590
Pro Glu Ser Gly Trp Thr Glu Glu Asp Gly Pro Lys Glu Gly Leu Ala
            595                 600                 605
```

```
Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
            645                 650                 655

Ile Leu Arg Leu Ala Thr Glu Val Asn Trp Asp Glu Lys Glu Cys
            660                 665                 670

Phe Glu Ser Leu Ser Lys Glu Cys Ala Met Phe Tyr Ser Ile Arg Lys
    675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
            725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 2
<211> LENGTH: 57497
<212> TYPE: DNA
<213> ORGANISM: Homo sapiens

<400> SEQUENCE: 2
gaagagaccc agcaacccac agagttgaga aatttgactg gcattcaagc tgtccaatca      60
atagctgccg ctgaagggtg gggctggatg gcgtaagcta cagctgaagg aagaacgtga     120
gcacgaggca ctgaggtgat tggctgaagg cacttccgtt gagcatctag acgtttcctt     180
ggctcttctg gcgccaaaat gtcgttcgtg gcaggggtta ttcggcggct ggacgagaca     240
gtggtgaacc gcatcgcggc gggggaagtt atccagcggc cagctaatgc atcaaagag      300 atgattgaga actggtacgg agggagtcga gccgggctca cttaagggct acgacttaac     360
gggccgcgtc actcaatggc gcggacacgc ctctttgccc gggcagaggc atgtacagcg     420
catgcccaca acggcggagg ccgccgggtt ccctgacgtg ccagtcaggc cttctccttt     480
tccgcagacc gtgtgtttct ttaccgctct ccccgagac cttttaaggg ttgtttggag      540
tgtaagtgga ggaatatacg tagtgttgtc ttaatggtac cgttaactaa gtaaggaagc     600
cacttaattt aaaattatgt atgcagaaca tgcgaagtta aaagatgtat aaaagcttaa     660
gatgggagga aaaacctttt ttcagagggt actgtgttac tgttttcttg cttttcattc     720
attccagaaa tcatctgttc acatccaaag gcacaattca ttttgagttt ctttcaaaac     780
aaatcgtttg tagttttagg acaggctgat gcactttggg cttgacttct gattacccta     840
ttgttaaatt agtgacccct cttagtgttt tcctgtcctt tatttcggag gacgcacttc     900
gaagatacca gattttatgg gtcatccttg gattttgaag cttataactg tgacaaaaaa     960
tgtgaaggga agagatttga acatgtggaa ggaaaagtga agtgcagact ataaacttcc    1020
aaaaagacaa gcccaaaata cacctaaacg ttatgtcaga ttattttgtt aaaatcagtt    1080
gttagtgacg tccgtacgtt aatagaaaaa agaatgcttc agtttggagt ggtaggtttc    1140
tagagggatt tattgtgaaa gtataaacta ttcagggcaa tgggactgag agaacagtgg    1200
```

```
gtagaaagga ccactgaagg aaaggaagag aattggaagg tagatgaaag aaggagcaag    1260
aacctgggga tgttttttcc ttttcacttg taatagtagt aacagaagca atggcagact    1320
ggcttttgtt tctactgtgt tagaatgaat tgacaggaca actgggccta ttattgtact    1380
gtgccagaat actgtaaaac aaaactaaac atactagctt ggtggcttgt aattaattac    1440
ttaagtggag attttattt ttttttatt ttttttttag acggagtctc actttgtcac     1500
ccaggctgga gtgcagtggc gcgatctcag ctgactgcaa cctcctcctc acaggttcaa    1560
gggagattct cctgcctcag cctcccgagt agctaggact ataggcatgt gccaccacac    1620
ctggctaatt ttgtattttt agtagagatg gggatttctcc atgttggtca ggctggtgtc   1680
aaaactctcg atctcaggtg aaccgcctgc ctcagccttc caaagtgctg ggattacagg    1740
cgtgagccac cgcgcccgtgc agtttttgt attttaata gagacagggt ttcaccatgt     1800
tagccaggat ggtctcgatt tcctgacctc aggtgatctg cccgctttgg cctcccaaag   1860
tgctgggatt acaagcatga gccaccgcgc ccggctcaag tggagatttt tatatggagt   1920
ccagttatac tcttttaat atataagttg agatgactaa tacaacttca atacaggggc     1980
tcatgagaaa tgtctgtaat atttaagtaa cttattgtct ctttctttt tttttaaga    2040 tgaagtctta ctctgttgcc caggcggaag tgcagtggcg tgatcttggc tcagggcaac    2100
ctctgcctcc tggtttcaag cgatcttcct gcctcagcct cccgagtagc tgggagtaca    2160
ggcgtgcatg accacacccg ctaattttt tatttttag tagagacggg gtttctccat     2220
gttggccggg ctggtcttga actcctgacc tcaggtgatc cgcccacctc agcctcccca    2280
agtgttggga ttacaggtgt gagccccgt gcccagccta ttatcttatt ctgaataaa    2340 gaattgtctg tgtggggaat agataactct ttctcatgca gcccctgcta gaaaatttgt    2400
tttctctagc agttggtctg tgcttatagg ctactctttg aaagcacaaa aaatttattg    2460
acttcttttt tttgggtttt ttttttttttt tgagacagag ttttgcccct gttgcccagg    2520
ttggagtgca atgcgcgat ctcagctcac cgcaacctcc acctcctggg ttcaagtgat    2580
tctcctgcct tagcctcctg agtagctggg attacaggca tgcgtcacca tgcctggcta    2640 atttttgtatt tttagtacaa atgggggttc tccatgttgg tcaggctggt ctcaaactcc    2700
tgacctcagg tgatccaccc gccttggcct cccaaagtgc tgggattatg ggtgtgagcc    2760
attgcgcctg gccagaaaat tcattgactt cctaaagatt tattaacttt ctgcattact    2820
tttttttttc ccctccatcg taaatataaa agggaatagt agagaaaatc attcagaatt    2880
ttatttttta gtgacattat ttagtgacat tttattagag tcacttagga acctgaggct    2940
gaataaagtt caggtaaaag taaaattagt tgagaagaga catctgccaa aagaaatcta    3000
tttttaactt cacttgctgt ctttcctaga ggaacagaaa tagtgctgaa tgtcctatta    3060
gaaatgatgg ttgctctgcc cgtctcttcc ctctctctca cacaatatgt aaactcatac    3120
agtgtatgag cctgtaagac aaaggaaaaa cacgttaatg aggcactatt gtttgtattt    3180
ggagtttgtt atcattgctt ggctcatatt aaaatatgta cattgagta gttgcagact     3240 gataaattat tttctgtttg atttgccagt ttagatgcaa aatccacaag tattcaagtg    3300
attgttaaag agggaggcct gaagttgatt cagatccaag acaatggcac cgggatcagg    3360
gtaagtaaaa cctcaaagta gcaggatgtt tgtgcgcttc atggaagagt caggaccttt    3420
ctctgttctg gaaactaggc ttttgcagat gggatttttt cactgaaaaa ttcaacacca    3480
acaataaata tttattgagt acctattatt tgctgggcac tgttcagggg atgtgtcagt    3540
gaataaaata gattaaaatc tattctcttc tgatgcttac attatagtgg tgggagacaa    3600
```

```
aatgggtata ataaatatta tattagatag cattaagtgc tgtggagaaa actaaagcag      3660
ggaggaagat aggagtgtgc aagccagaaa ggttgcaatt aaattgagta gttcaggaag      3720
gcttcaatat ggatgtgata tttgagagac cggtggaagt caaggagcaa gttgtgaggc      3780
tatttaaagg tattccttgg cttacagaaca atatacgcaa agactattaa atggaagcat     3840
acctgacatg ttaaaggact atcaaggagg ccagtttgtc tagaggctga aaaggaaaga     3900
gtaataggag atgaggtctg agtgaaaaca cgtaaatcct tgtgggccaa ggtaaaatct      3960
ttagcttttt ttctgaatat ggtgggatac tgttagaggg ttttaagcag aggttacgtg     4020
gtgtggtgag tttttttttt ttaatccttt gtctttctgt gtggaaaata gcaggacagg     4080
gcagaagcag tctgtcctgc agactgcttg gtcgcagtag agatgtaaga agcagtgaga    4140
ttctgggtta attatggagg caaagttctc agaatttgct gatataggt atgagagaaa      4200 gaggaatcag gaatgatttc aaggttttgg tctgctaaat ggaaggagtt gccatttact      4260
aagatgggaa agactatgaa agaagcagat tttcagagag atcagaagtt cattttgggg    4320
catgttcaat ttaagatgcc tgttagttgg atgtttatgt gagtttggaa tgcagggtag     4380
agatttaggg atgaatattt ggtagttgtc tgcatttaa tggtattaaa agccacgaga      4440
aggatgggca tggtggctca cacctgtaat cccagcactt gggaggcca aggcgggcag     4500 atcacctgag gtcgggagtt cgagaccagc ctgaccaaca tggagaaacc ccatctctac    4560
taaaaatata taattagccg gcgtggtgg cacatgcctg taatcccagc tactcgggag    4620
gctgaggcag gagaatcgct tgaacctggg aggtggaggt tgcgatgagc cgagatcgca    4680
ccgttgcact ccagcttggg caacaagagc aaaactccat caaaaaaaaa aaaaaaaaa     4740 aaaaaaagcc ttgagactca cctgaaaaga tgctcaacat tattggtcat taggaaaatg    4800
aatgaaaacc acaatgagat accacttcac acctattagg atggctatta tcaaaaacaa   4860
aaacaagtgt ttgcaaggat gtagagattg gaattcttgt gtattgctag agggaatgta    4920
aaatagtgca gggtgctgtg gaaaatgctg tggtgattcc tcaaaaaatt aaacataatt     4980
atataatcca gtaattccac ttctgagtta ttcccaaaag aagggatgca agcagatatt    5040
tgtacactca tattcatggc agcattattt acagtagcca aaaggtgaaa gcaacctaag     5100
tgtccgtcag tggatgaatg gataaacaaa atggaataat ttcagcctta aatagaaata    5160
aaatgttgac acatgttgca acatatacga accttgaaga catcatgtta agttaaataa     5220
gttggtcact aaaggacaaa tattgtatga ttccccttat gaggttccta gagtagtcac    5280
attcatagag acagtagagt ggtggttgcc cagggccggg gggagcgagg agaatggaaa    5340
ttattgttta ttgggtacag agtttctgtt tggggaagat gaaaaaattc tggagatgga    5400
tcatgatgat agttaacaca gcagtgtgaa tatagttaat ggcacagaac tgtacattta     5460
aaaatggtta agatggaaaa ttttctgtta catatatttt actgcaattt ttttaaattt     5520
tattattata ctttaagttt tagggtacat gtgcacaaca tgcaggtttg ttacatatgt    5580
atacatgtgc catgttggtg tgctgcaccc attaagtcat catttagcat taggtatatc     5640
tcctaatgct atccctcccc cctcccccac cccacaacag tcccagtgt gtgatgttcc      5700 cctttctgtg tccatgtgtt ctcattgttc aattcccacc tatgagtgag cacatgcagt    5760
gtttggtttt tgtccttgt gatagtttgc tgagaatgat ggtttccagc ttcatccatg     5820
tccctgcaaa ggacatgaac tcatcatttt tgtggctgc atagtattcc atggtgtata    5880
tgtgccacct tttcttaatc cagtctatca ttgttggaca tttgggttgg ttccaagtct    5940
```

```
ttgctgttgc gaatagtgct gcagtaaaca tacgtgtgca tgtgtcttta tagcagcatg   6000
atttataatc ctttgggtat atacccagta atgggatggc tgggtcaaat ggtatttcta   6060
gttctagatc cctgaggaat tgccacactg acttccacaa tggttgaact agtttacagt   6120
cccaccaaca gtgtaaaagt gttcctattt ctccacatcc tctccagcac ctgttgtttc   6180 ctgactttt aagatcgcca ttctaactgg tgtgagatgg tatctcattg tggttttgat    6240
ttgcatttct ctgatggcca gtgatgatga gcatttcttc atgtgttttt tggctgcata   6300
aatgtcttct ttcgagaagt gtctgttcat atccttcact cacttttga tggggttgtt    6360 tgtttttttc ttgtaaattt gagttcattg aaaaattaga atttttttt ttttcccttt    6420 tttagaggca aggtctcact ctgtcgccca cactggagtg cagtagtgta agcatagctc   6480
actgtaacct tgaactcctg ggctcaagca attctgtcat ctcagccagc tgaagtagta   6540
actgtaggtt cacaccacca tgcctatttt tgttttgta gaaatagggc cttgctttgt    6600
tgccaaggct ggtcttgaac tcctgacctc aagcagtcct cctgtctcag cctcccaaag   6660
tgctgggatt ataggtgtga gccactgcac ccagccttgg agattttaa taaagaagct    6720 tgtcaattaa acaaacaaca aaaagccctg agactgaatg agataatcaa gagagtatgt   6780
gtagatagag aagaggtcca aggaaggagt cttgggtgac tctgatgtca agtgaggaca   6840
tgaggcagaa acagcagtga ctgagaagga gccacctagt aagaaaggag gaacaccagg   6900
acagtgtggt attctggatt ccaaacaagg aagttactgc taatttaaa gctcttctca    6960 ggctgggcat ggtggctcac acctgtagtc ccagcacttc gggaggctga ggtaggtaaa   7020
tcacttgagc tcatgtgttt gagaccagct tgggcaacat ggtgaaacct catctctact   7080
aaaaatataa gaaattaagg ccaggtgtgg tagttcatgc ctgtaatccc agtgctttgg   7140
gaggtcaagc cagccagatc atttgagatc aggagttcga gaccagcatg ccagcatag   7200 tgaagcccca tctctactaa aaatacaaga aaaattaac caagcatggt ggcgcatacc    7260
tgtaatccca gccactctgg aggctgagac atgaaaattg cttgaacccg ggaggcggag   7320
gttgcagtga gctgagatct cgccactgca cttcagcctg ggtgacagag caagactctg   7380
tctcaaagga ggttgcagtg agctgagatc tcgccactgc acttcagcct gggtgacaga   7440
gcaagactct gtctcaaaaa aaaaaaaac aaaaaccaag aaaagaaaaa aaaactcttc    7500
taagaggatt ttttttcct ggattaaatc aagaaatgg gaattcaaag agatttggaa     7560
aaatgagtaa catgattatt tactcatctt tttggtatct aacagaaaga agatctggat   7620
attgtatgtg aaaggttcac tactagtaaa ctgcagtcct ttgaggattt agccagtatt   7680
tctacctatg gctttcgagg tgaggtaagc taaagattca agaaatgtgt aaaatatcct   7740
cctgtgatga cattgtctgt catttgttag tatgtatttc tcaacataga taaataaggt   7800
ttggtacctt ttacttgtta aatgtatgca aatctgagca aacttaatga actttaactt   7860
tcaaagactg agaattgttc ataaataaac tattttacct gcagagacct ctgatatatg   7920
tttcttgatg gaagtaccca gtaccaccta tgaagttttc ttgtcaaaaa atcaaatgtg   7980
aatctgatca ttacttagat ctaagtacca atatatgaaa aatataggag acaaggaagc   8040
atggtaaatg atactgagat tgggagacta catggaaaaa gacttgttcc cttcaacaga   8100
tagacagcag ggaaaaaaga atagagaaag gagtaaagaa cctgtagatt aaaagacatt   8160
taagggacat atgaaccagg tccagtgtat agatcttacc taaatcctga tggagcaaac   8220
tataaaaaaa ttttttgag acaaatgttt gaatacaggt tgactatttg atggcattaa    8280
ggagaaatta tgaattatct tggtataaga atattgtcat gggtttttt tttgagtcc    8340
```

```
ttacctgtta agatacatac taaaatatttt gtgggtaaaa ttatatgacg tataggagta      8400
tatgatttag aaaacggatt aaaatataaa aggataaaat aggatcttat attttgtgac      8460
tcacttcctg ttggatatct ttctacccag taaatatagt cctatctagg ttttaatggc      8520
tacatgtatg tactgtagtt tgtttaaatg gtttcctatt gaacatttat gctctttgcc      8580
attttttcct gtttaacgtt ctgttttttt ttttgttttt ttttttttttt gagacagtct      8640 tgctctgtta tccagactgg agtgcagtga catgatctca gctcactgca acctctgcct      8700
tctgggttca agctattctc ctgcctcagc ctcctgaata gctgtgatta caggcgtgca      8760
ccactatgcc cagctaattt ttgtattttg ggtagagaca gggtttggcc atgttggcca      8820
ggctggtctt gaactcctga ccttgaatga tctgcccgcc ttggccttgc aaagtgctgg      8880
ggttacaggc atgagccacc acgtctggcc ttgtttaagg tcctgatgag tattcttata      8940
ggtacactgt gtttcgttta attatttcct taggataaat ttatagaaat aacattcctt      9000
ggtaaaagaa tacatatttt aaaaactgta ttagtttcct gttgctgtca aaaaatttcc      9060
agaaacttag tggcattaaa caatacaaat taattattct acagttctgg agatcagaag      9120
atacgggtct tactaggcct cactaggcta aaatcaaggt tttggcaggg ctgtgttcct      9180
ctatggaggt tccaagggac cagagaaact actttacagt agttatttta agggaatgaa      9240
agtgaagatg gggttgggca gtcaaagagg ctgttacttt tcattttttgg cctttcagta      9300 gtttgaattt ttttatcata tacatgtatt actttaattt ttaaaaagta aaaagcagct      9360
gtgattcagt ctctgtaatt tagatcaatt tacatcaaac tagggtggtc tcatgtgttg      9420
tcttgctcac agtgaccact agattattcc aagaagggac aatttccaag acttggttta      9480
cactgagacg gctcctgatt ttaaggatac cttagatcaa actctaggaa ggcagtttca      9540
ttttggcctt gcagttccct gggtcatttt ccaagcccat ggcctcctgg agtcttcgcc      9600
tagctgtagg ttatctttgt ggctattatt tcactgtaat tatacaggaa gatttattga      9660
gggatttctg tgtaccagcc gtggttctca gcactttgta ctttgtat taactctgac       9720 tcctgacagt aactctacag aggttctgct gttacccagt tttacataga aacatggcca      9780
gcggacgcag ttagaaaatg gcaaagtggg gattagaaac taggcagttt gactccagag      9840
tctgtgcccc tgtccacttg gctccactgc tggggaagag gcctctgaag cagcaggacc      9900
atctgctgtg ccgtgtgtag tggtactcta tcttcctggt gtgatgttgt gttctacttt      9960 gcatttcat gtctttcctt atacaggtct caaaatcatt tactttttt tttttttttt       10020 tgagacggag tctcactctg ttgcccaggc tagagtgtag tggcatagtc tcactcactg      10080
caacctccgc ctccgaggtt caagtaattc tcctgcctca gcctcccaag tagctcggat      10140
tacaggcaca tgccaccaca gctagcaaat ttttgtattt ttagtagaga ttggtgtttc      10200
accatgttgg ccaggctgtt cttgaactcc tgacctcagg tgatccaccc acctaggcct      10260
cccaaagtgc tgggattaca ggcgtgagcc accccaccca gccttatatt ttttaatgat      10320
gcacattagc tcaattacat aaaccaggga aatccagcta ggacctggtg atttctgagc      10380
ctgacccatg tgactttcaa tgaactgaac ttgccacagc tgtatttact gtctactgag      10440
atgctgtcac acagaccccg tcatagcaca gttcctgagt tacatcttta catactgtag      10500
tatccttctt gtgaaaaaag atacagattc caaggtctg agaaaccaat cttggttata       10560
aaggggaaaa atggtcatgg gtttttaaaa tttgttttgt cttaattgca tttcaaattt      10620
acatttctaa atgaataatt gcttatataa agcagttttg attaacaata taaaacacta      10680
```

```
tctatttgga gtgattcctt tacccatttc tgaaggcaag ttttaaaaat tactagaaga   10740
cacttcattg agaatattat taaacatgcc tatagttcta ccacctcaac acaattgctt   10800
attaacacat taatgttttg gtgtgttttg gacttttttaa tatgtatttt tcacttgttc   10860
tagtaattat gctacagatt gatcatttct ttttcaacat gtcatcaaag caagtgagca   10920
aagtgctcat cgttgccaca tattaataca aaatggaagc agcagttcag ataacctttc   10980
cctttggtga ggtgacagtg ggtgacccag cagtgagttt ttctttcagt ctattttctt   11040
ttcttcctta ggctttggcc agcataagcc atgtggctca tgttactatt acaacgaaaa   11100
cagctgatgg aaagtgtgca tacaggtata gtgctgactt cttttactca tatatattca   11160
ttctgaaatg tatttttttgc ctaggtctca gagtaatcct gtctcaacac cagtgttatc   11220
ttttttggca gagatcttga gtacgttttc ttttctcctt attgataaat tgataatcct   11280
caaggatgat tattaggtga tactcttact tcatggattc ttaaaagata tgatttaaca   11340
tattacaagt gcctagcaag gtgtctgtta cacgtaggta ttttaagtaa atggtagctg   11400
ctgatgtaat ttctgcccct ttgcccttca gttggggtat tgctttggac cgattagagg   11460
gctgtggctg ggatgctaaa ggttcatgtt tccttagctg gctcctgagc caccagctcc   11520
caccacctgt gtatacctgt gctagtttgc cttcccacaa gtagctgctg gctatctgtt   11580
atgctggtac agttttcaga aactgatgaa tggcctttga acagaacaaa atgagattc    11640 agaataacaa aattgcacct tgttttttat aagcactggc cattcactag ttgaagactg   11700
gtaggaatac ctaattcatg ccaaaagaaa gataattttt aaaaatcaca caggttgttt   11760
gtagattaaa agggaaaata ggctaggtat agtggctttg cctgtgagtt tgggaggctg   11820
aagtgggagg attgcttgaa gtcaggagtt tgagaccagc ctgggaaaca gagcaagacc   11880
ccgtctctac agaaaatttt taaaaaatta gctgggcatg gtgatgcata tctgtagtct   11940
tagctactcc ggaggtggga agattgcttg agcccagcag tttgaggctg cagtgagctg   12000
tgattacacc actgtactcc aaccttaaaa taaataaata aataagggaa atatatcttca   12060 acaaaggata gttctgtctg tttctcagtc ttcctcaaca gataaatgtg tgaagtaatg   12120
gaaggtggag atttcagatt acacaacatt aatgctaagg gcgtttgact ctgtgtgaat   12180
tctaattgcc ctagatctag acgggctgat actattagaa tcccctgtca ctaactgaag   12240
acagagttgt aagttaatgc cttcctagat agcctagatt gtggtatgct gctgcatgct   12300
aaaatggctc cccttccata gcaggatgaa atagagtcat tatcttggca accagcccct   12360
gccaatgtgc tctcagtctg ccttttccagc cccttctctc tacctattcc cagctgccat   12420
gtattctaaa gcctctatgc tttcattttt gttttgcct tcctggatgg tctttcctgc     12480
tgtctccacc tgaaactatt cctctctaaa gaacagatga attgccatct ctctgggatg   12540 cttttacccca ccctcactcc cacctcaggc tgaatggacc cttctctaga tcgcttagca   12600
tattgttcta cagttaggta aaaagtctac ctatcactag atcaagagct ttgtttttttt   12660 ttattaattt aattttcttt ttttttttttc tttttttttt gagacagagt ctcgctctgt   12720
cgcccaggct ggagtgcagt gcacaatctt ggctcactgc aagctccgcc tcccaggttc   12780
acaccattct cctgcctcag cctcccgagt agccgggact acaggcgccc accaccacgc   12840
ccagctaatt ttttgtattt ttagtagaga cggggtttca ccatgttagt tagccaggat   12900
ggtctcgatc tcctgacctc gtgatccacc cacctcggcc tcccaaagca ctgggattac   12960
aggcatgagc caccgcgccg agccccaaga ccttttcttta ttaccagggc ttccacagac   13020
ctgacacatg gtagttcctc aataaataat tgcagaatta ctgaaaaatt ttactgttaa   13080
```

```
cttaggcagt ggtaaaacca ttgtttggta gctcagaact cagcaagtaa atagcaacat     13140
ttgctggaag aacagatagt tttcaaatc caattcaagg actgggtatg gtggctcatg      13200
cctgtaatcc cagcactttg ggaggccgag gcaggcgtat ccaggagttc gagactagcc    13260
tgaccaacat ggtgaaactc cgtctctact aaaaatacaa aattagccag gtgtggtggt    13320
gggcacctgt aatctcagct acttgggagg ctgaggcagg agaatcgctt gaacctggta    13380
ggcggaggtt gtagtgagct gagattgtgc cattgctctc cagcctggga acaagagca     13440 aaactccgtc tcaaaaaaaa aaaaaatcca attcaaatga ttatggaagt agtggagaaa    13500
taaacaggaa aatgataaat aattaagata atatataata tggctatatt ttaatctatt   13560
gttgatatga ttttctcttt tccccttggg attagtatct atctctctac tggatattaa    13620
tttgttatat tttctcatta gagcaagtta ctcagatgga aaactgaaag ccctcctaa     13680 accatgtgct ggcaatcaag ggacccagat cacggtaaga atggtacatg ggagagtaaa    13740
ttgttgaagc tttgtttgta taaatattgg aataaaaaat aaaattgctt ctaagttttc    13800
agggtaataa taaaatgaat ttgcactagt taatggaggt cccaagatat cctctaagca    13860 agataaaatga ctattggctt ttgtggcatg gcagcctgcc acgtccttgt cttttttaag   13920
ggctaggaga ttcttttattg ggatggcaaa agtcaatggc agggtagttg tcattgaaag   13980
aagattaagc ttgaccccag aaggcatggg ttagagccca gccttgtcac tcaatggttg    14040
tatgtccaga ggcaagtcac ttaacatccc ttaaccccag ttttctcatc tgtcaaatga    14100
agcaaagaat acttgccctc ttgacttaaa gggtgtctga tgagacatat gactgtatca    14160
ttagctggga gaaagtccat cgtgctgcct atgtatagtg cctcaagttg gtctctttcc    14220
cttctatgat tacacaaagc actccgctgt catgttatcc atcccgcccc tccattccaa    14280
gtcccatcta gagcacatct tcttgaagtc cactgtaacc tgcctaatcc tggatgtgac    14340
gagccaggca ggaggcagaa aagaatgtgt gttttgcaat acatgttaag agacatcttg    14400
ggctgggcac ggtggctcac acctgtaatc tcagcacttt gggaggctga ggagggcgga    14460
tcatctgagg ttgggagttc gagaccagcc tgaccaacat ggagaaaccc catctctact    14520
aaaaatacaa aattagccag gcgtgatggc gcatgcctgt aatcccagct actcaggaag    14580
gctgaggcag gagaattgct tgaacccggg aggcagaggt tgtggtgagt tgagatcatg    14640
ccactgcact ccagcctggg caacaagagt gaaacagggt ctcaaaaaca aaacaaaca     14700 aacaaaaaaa atcttttacc acggtgacca ccatgtgatt tccaagaact tcaaatgatc    14760
taagaaattt tgtgattatt actagtttga aaaatacttt ttttttttt gagacaaagt     14820 ctcactctgt tgcccaggct gaagtgcagt ggtgtgatct cagctcactg caatcactac    14880
ctcttgagtt caagcagttg tcctgcctca gcctcttgag tacctgggat tacaggcatg    14940
cgtcaccatg cccggctaat ttttgtattt ttagtagaga cagggtttca ccatgttggc    15000
caggctggtc tcgaactcct gacctcaggt gacccaccca ccttggcctc ccaaagttct    15060
gggattacag acgtgagcca ctgcacccag cctgaaaaat atctttgaat gccatgtgat    15120
actatacttg tcagtttaca tgtgtgtccc actaaatcat gtactctcct gagcaggatc    15180
atgctttgtc ttcatatttt ctgtacaaag caaagactct gacacaaagc tagccccag     15240 tgcatagttg agaaatcagt gaatgaatgt gggaggcagg aaaaatgtcc tttaattctt    15300
ctgttaatgc tgtcttatcc ctggcccag tcagtgctta gaactgtgct gttggtaaat    15360
ataattggat tcactatctt aagacctcgc ttttgccagg acatcttggg ttttattttc    15420
```

```
aagtacttct atgaatttac aagaaaaatc aatcttctgt tcaggtggag gaccttttt     15480
acaacatagc cacgaggaga aaagctttaa aaaatccaag tgaagaatat gggaaaattt    15540
tggaagttgt tggcaggtac agtccaaaat ctgggagtgg gtctctgaga tttgtcatca    15600
aagtaatgtg ttctagtgct catacattga acagttgctg agctagatgg tgaaaagtaa    15660
aactagctta cagatagttt ctggtcaagg tttagccacc aattttgcag tttctctcat    15720
ctccccagga aagagcagtt ggtctttaga tcaatgagag ctcttttatg cagacaaaa     15780
caaagtgact ctagccaact tgagctaaaa agaaatttag tggaaggcta ggagttacca    15840
catgaagtgt gtgcagctgc cccttggaga gaataagaac cagggtgcct ctgggactta    15900
acatcattac tgtactccag ttgttttcat tcttttcctg actttgctct agagtcagtt    15960
tcctaacaga gtacattcga tgatcatgtg cccatatctg tggggagaag atttcttgat    16020
tggcagtctt actaagggtg catatcaagt agaatggaat agaggtagtt tcctaaagga    16080
agatgagagg ctgttaccag gaggaggaga agggattcag gacagatgaa acaacgtta     16140
tatccatgat agacttacgc tgctggtaca gatggtacag gtggcttcag tataggctct    16200
ccgaacccac atatcattga ttatgatagg gatatgttaa ctatttttca gtgtatatat    16260
gtatatgtgt gtgtgtatat atatgtatat gtatatatat atgtatgtgt atatatgtat    16320
atgtatatat ttatatatgt atatgtatat atttatatat gtatatgtat atatttatat    16380
atgtatatgt atatatattt atatatgtat atgtgtgtat atatatattt atatatatgt    16440
atatgtgtgt atatatatat attttttttt gaaacggaat ttcgctcttg ttgcccaggc    16500
tggagtgcaa tggtgcgatc tcagctcact gcaacctctg cctcctgggt tcaagcgatt    16560
ctcctgtctc agcctcccga gtagctggga ttacaggcac ttgccaccat gcccggcaat    16620
tttttttttg ttttttttta gtagagaggg ggtttaatca ttttggccag gctggtcttg    16680
aactcctgac ctcaggtgat ctgcctgcct tggcctccta aagtgctggg attacaggcg    16740
tgagccacca tgcctggcca ttttcagta tttcttttt tttttttttt tttttttt       16800
ttgagacaga gtttcactct tgttgcacag gctggagtac aatggtgtga tctcggctca    16860
ccgcaacctc tacttcccag gttcaagcaa ttcgcctgcc tcagccttct caagtagctg    16920
ggattacagg catatgccac catgcccggc taattttgtg ttttttagtag atgggggtt    16980
tctccatgtt ggtcaggcta gtctcaaact cccgacctca gatgatcctc ccgccttggc    17040
ctcccagagt gctgggatta ctggcatgag ccagcgctcc tggcccattt ttcagtattt    17100
ctaaaaaaaa tctaaagtgg gtcaaacatt tcaccttaat agaatgacag gtttgtacat    17160
caagtttctt tgcttttttct tggaatttta tactttttt tttttttgg agacagagtc     17220
ttgctgtgtt acccaggctg gagtgcagtg gtgcgatctc agctcaccac aacctccacc    17280
tccaggttga agcaattctc ctacctcagc ctcctgagta gctgggatta caggcacatg    17340
ccaccacacc cggctaattt ttttttttttt tttgtatttt tagtagagac agggtttcac    17400
catgttgtcc aggctggtct cgaactcctg acctcaggtg atccgccat ctcggcccac     17460
caaagtgctg ggattacagg cgtgagccac tgcacccggc cttttcttg gaattttatc     17520
aatcagtgtc agaatattca ttacctccta aaaataaagg agttctagtt ggctgttttg    17580
attctaggtg tggtaaagtg aaatattgtt acttaataaa tgcattttgc tagacacaat    17640
ccttcggttc acgagctctg tagagaaaag agaaataacc gccaaccaag aaaagattgg    17700
gagatactag aataagaccc aggggcagga agaagccagt gagaaggagg gcatgttgag    17760
agctctgaga gagaataaaa gcaggggttg ttggagctag cttctcaaga tgtccttgag    17820
```

```
gcaaaccaga cctttgggac actctgaaaa taaaactgaa agtgaagaga ttgtgggccg  17880
aatgtggtgg ctcacgcctg taatcccagc actttgggag gtcgaggcgg gtggatcacc  17940
tgagatcagg agttcgatac cagcctggcc aacatggcga aacgccatct ctactaaaaa  18000
tacaaaaaaa attagctggg cctggtggca ggcgcctata atcccagcta ctcgggaggc  18060
tgaggcggga gaatcgcttg agtccaggag gcggaggttg cagtgagctg agatcgtgcc  18120
attgcactcc agcctgggca acaagagcaa aactctgtct caaaaataaa taaaaataaa  18180 taaaaagag atagtggcgt gatatccttg attctatcag caacctataa agtagagag  18240 gagtctgtgt tttgattcag tcacctttag cattttattt tccatgaagt ttctgctggt  18300
ttatttttct gtgggtaaaa tattaatagg ctgtatggag atatttttct ttatatgtac  18360
ctttgtttag attactcaac tccactaatt tatttaacta aaaggggct ctgacatcta  18420 gtgtgtgttt ttggcaactc ttttcttact cttttgtttt tcttttccag gtattcagta  18480
cacaatgcag gcattagttt ctcagttaaa aaagtaagtt cttggtttat ggggatggt  18540 tttgttttat gaaaagaaaa aaggggattt ttaatagttt gctggtggag ataaggttat  18600
gatgtttcag tctcagccat gagacaataa atccttgtgt cttctgctgt ttgtttatca  18660
gcaaggagag acagtagctg atgttaggac actacccaat gcctcaaccg tggacaatat  18720
tcgctccatc tttggaaatg ctgttagtcg gtatgtcgat aacctatata aaaaaatctt  18780
ttacatttat tatcttggtt tatcattcca tcacattatt ttggaacctt tcaagatatt  18840
atgtgtgtta agagtttgct ttagtcaaat acacaggctt gttttatgct tcagatttgt  18900
taatggagtt cttatttcac gtaatcaaca ctttctaggt gtatgtaatc tcctagattc  18960
tgtggcgtga atcatgtgtt ctttcaaggt cttagtcttg aaaatattta tagtgtagta  19020
gaactatttt atcctccaat gctccttctt ttccttgtat ttccattatc atcactttag  19080
gatttcactt atttatcatt caacatttat taattgcctc tcatattcca ggctttgtgc  19140
tagaagttag ggatataaag acaaataaga tatttcctgc ccttaaagac tagattcgtg  19200
ttgctaagtc ttcattatca agaaaagcat aagtggggaa aagtgcttgc attatggatt  19260
cctcatagtt gctcccctct gcatgtaaaa atcaccattt ccatcataga ttcctagcgg  19320
tctcaggact ttataaagcc caaagtgcct atgtcataat atgaggaaaa atactgagac  19380
ccttccatat atgggaggta tatggatgag acagctcctg acttcacttt tcccagaaat  19440
ctgaaaagca gcagcagtca ttccagagcc cagtttctac tttgaagggc agattattta  19500
ttctttgagc taacctgact gaggaacaat tagtttgctt ttaatttact attttctttt  19560
tcttttcttt tcttttttga dacagagtct cactctgttg cctaggctgg agtgcagtgg  19620
ctcaaacttg gctcactgca agctccgcct cccgggttca cgccattctc ctgcctcagc  19680
ctcccgagta gctgggacta caggcgcctg tcaccacacc cagctaattt tttgtatttt  19740
ttagtagaga cggggtttca tcgtgttagc caggatgatc tcgatctcca gacctcgtga  19800
tccacccacc tcggcctccc aaagtgctgg gattacaggc gtgagccacc gtgcccagcc  19860 actatttct ttctaattgt taatgaatta atttttaaa actgtgctcc tagagcgaag  19920
ggagagctct gtttacagtg taacttttca gagcttcttt aactagattt taagatcaga  19980
attagttgtt gtgaaatctt agggactgta caagattaga aatcctctat agcagcattt  20040
cccaaagcag gcttccagaa cactagcctc atgaggcatt tgggaaaaaa agagtttgct  20100
ggttcagtgt gtatgggcag tgccacaagc cgtaccctcc gttgaagaca ctcattccac  20160
```

```
acattactgc ataaaaagct tccaccagcc attcggcaaa cttattgagt gtctgctatt    20220
tcctgggtat tgtgctatat ggtagggtta tagtagtgaa caaagaagaa atgatgcctg    20280
ctctcagctg actttgcagt tggaaagaca catgaaataa ttacgccatt cattagcaga    20340
ttgtgctaga tgcctcactg gaaaataaaa ggacatgatg gaaaactctg tagggtcaga    20400
gaaagggatc attagagaag gttctttgaa gaaatatttt ttgaaatatg aaggataaat    20460
aggaattaac taggtaccaa taggttagga gtagagcttt ccagacagag ggactagttc    20520
ttgggaaggt ctccagacag aaataagtgt ggcttgtctg aggacctctt attcgcctat    20580
taaccttccc tccccagtaa acactcctgg gaacaacaca cattgtagaa ccacgttgtg    20640
gtgctgttca gtatagcaag taattcagca gagataagtt cttggaatct catctttggg    20700
atttagttac taagatacat tcaagtttga gcaaaataag gtctcagagc ttggattcat    20760
tgttctgttc cagcaattag agcagtacct ggcacatagc acaagtgctt gaaaacactg    20820
actgagtagg gtaggtgggt gagtgggtgg gtgggtgggt gggtggatgg atggatggga    20880
ggatgggtgg gtgaatgggt gaacagacaa atggatggat gaatggacag gcacaggagg    20940
acctcaaatg gaccaagtct tcggggccct catttcacaa agttagttta tgggaaggaa    21000
ccttgtgttt ttaaattctg attcttttgt aatgtttgag ttttgagtat tttcaaaagc    21060
ttcagaatct cttttctaat agagaactga tagaaattgg atgtgaggat aaaaccctag    21120
ccttcaaaat gaatggttac atatccaatg caaactactc agtgaagaag tgcatcttct    21180
tactcttcat caaccgtaag ttaaaaagaa ccacatggga aatccactca caggaaacac    21240
ccacagggaa tttatggga ccatggaaaa atttctgatc cataggtttg attaaacatg     21300
gagaaacctc atggcaaagt ttggttttat tgggaagcat gtataatttt tgtcctaagt    21360
ctgtgctcag ccctcccaca tgtgctcatt gctggttgac tgttggagtc tggttcttac    21420
ctctaagagg aagcccagga gagggcataa agccagcaca ctgtcctcac ctgatggtgt    21480
cagagtcctt acgagtaagc cctagccaga acattgctgg aagagatcaa gggccactgt    21540
ttgaaattgc acagcaggat acggaaaagg ggtaccttag gtataggcat tgtcattaaa    21600
gaaattgcta agatacttga gattttcctg tttaaggaat gagctttatg atacaaagag    21660
cagttctaaa aattagggag ggaattaact aaattaatta ggatatttct caaattcctt    21720
tacagttttt gtctctctgc tgatatagtg tttacatgat tgttatttac taaacaaatg    21780
ctattttgta ttgtgctcct tataacttaa ttgtttatta caaggttttg atggtgacct    21840
accaacaaca agtaatccca aacacagtct gaattttttg ttttccatcc agaaataaga    21900
tgaatctttc catttccgtg ttttcagttt tcatcatttt tatcctatag gttacttatc    21960
tttattttaa agcatttcat aataatttta tagtttttgt tttgtttgct tgtttgctgt    22020
tggaaatgga atattccctc cttccattta gactgctaac cagctgtaaa tgtttcaaaa    22080
tatgcatgtt ttacagcagt tgttcaaagc aatacaggaa cagtaaggac agagccagtc    22140
attttacaac cacattctgt taaactgatg tctattagca gggttttcc tattttatta     22200 ggaaggactt acacctgata tataacaaag cttgttttaa tcaaggctca gaaaatgttt    22260
ttcattagtt ttttcctaa ccatgaagaa taactgcttt gtaacacaca tgctggctat     22320
aaagcagaca aaaaattcac tgtaggtgct gcctgactgg cctctgtccg tgtttctgtt    22380
ggggctgctt accacagcct ctgcattatc attagctagt gtgttcacaa taccaagttc    22440
ccagtagcaa agaaaggtca agctcttacg catgccattc atttatctac actgtgcagg    22500
cgcactcagg tggcagggac aaagaccact cctttggcgc atctcaagtt cagaattctc    22560
```

```
agtagagggg ctccagctgt cctttttgtca ggtgcccatg cctgctccag gcctgtgtgg    22620
tcaggacacg tgttacagag tacagtgaca ttaatgatgg ggccatggat atggtcagca    22680
ctcagaggat gttagtctct tcattgataa agtcacaacc acttttcctg ttggaaataa    22740
aaagatttga cgtatccttg tctacagcaa cacaggacaa cagataatca gcaggtcatc    22800
taaatctgtt cagagagaaa ggagagctgt ttcctgaaaa tacatcttcc cctgattta    22860 gtcttatttt tttctgcctt tattgctttc taccctcttc aaaccagcct catttcctaa    22920
attaccttga atatgcattg acacttgtac tgcctgaaat tctggaaaac tcagtatggc    22980
tactccaccg tcagaacttc ctgagcaaag ttagttgctc tctcggctca ctgttttgtt    23040
ttgttttgtt ttcctgcctc aggtttattt gtacaaatag cacaggagga ccagccccat    23100
gcagatggta gccaggggc gggggtaggg ggtcacacca gtccttctgt cctcatgttg    23160
gcagagatat ctactctgaa gcctttgtag gggcctgggc acctttggga gcctgagctg    23220
gaactgaagg tggagctgca gcctgggcct tggtttgatc cttggccttg ccttttggcc    23280
ggcacagcct gagccccttg gcaatacggg cacgagcacg cttcccaagc ttgggatggg    23340
caatgtaggc aagtcgatcg agcttgcggc tgacacccctt tgggatcttg ggcttaacct    23400
ccttgggctt tacgagggcc ttgatagcct cggcacgtgc actcatggcc ttggcattgt    23460
tggcctgcat cttctttagg cccttcttgt tgtgcttctt ggcaaagtgc atgttcctca    23520
ggaacttggg gtccaccccc ttaagagatt cgtatctttg tgatcggggt ttcttgatac    23580
catttctgtg ccatttttcgg gactggttgt gtgtggtgtg gttcttggac ttcgccatgt    23640
ctacacctta agccgcggct cccgaagcac ctagaaccgg aagagttggc tcactattta    23700
gcacacacac acgtctataa tagtgctggc cacttggggt tggaattagt ttatttatca    23760
gcatgttgtc tcccagcact tggtgtgtgt gatatgcagt atgtatttgc agaatgaaaa    23820
gtctgagggc tgacatcata tttcccactg tgcccagaaa gagcacagtt agtccacatg    23880
agctaatggg ggcaaaggga agtgaggagg gagaatgtac tgccttatca tgttttctat    23940
tacttggctg aagtaaaaca gtcccaagcc gatagtaaga tagtgggctg gaaagtggcg    24000
acaggtaaag gtgcacccttt cttcctgggg atgtgatgtg catatcacta cagaaatgtc    24060 ttttcctgagg tgatttcatg actttgtgtg aatgtacacc tgtgacctca cccctcagga    24120
cagttttgaa ctggttgctt tctttttatt gtttagatcg tctggtagaa tcaacttcct    24180
tgagaaaagc catagaaaca gtgtatgcag cctatttgcc caaaaacaca cacccattcc    24240
tgtacctcag gtaatgtagc accaaactcc tcaaccaaga ctcacaagga acagatgttc    24300
tatcaggctc tcctctttga aagagatgag catgctaata gtacaatcag agtgaatccc    24360
atacaccact ggcaaaagga tgttctgtcc cttcttacag gtacaaggca cagttttcct    24420
tcatttattc actaatttag cagaacctca ctaagagcct cctatatgcc aggctctgcg    24480
ttagcaataa aaggaatgcc atgcctcacc ccatcaggag gtgctgatag cttgtaggcg    24540
gagtggaaac agatgtgctc tagaggctct aaatattact tctgctgggg tcagttggga    24600
agccacaaca gctactgttc atcttccata aaagacaatc agccgggcac agtggctcac    24660
acctgtaaat cccagcactt tgggaggctg aggtgggtgg atcacaaggt caggtgtttg    24720
agaccagcct ggccaacgtg gcgaaaccct gtctctacta aaaatacaaa aattagccag    24780
gcatggtggc gggcgcctgt agtcccagct actcggagg ctgaggcagg agaatcgctt    24840
gaacctagga ggtggaggtt gcagtgagct gagactgtac cactgcactc cagcctgggc    24900
```

-continued

```
gacagagcga gactccatct caaaaaaaaa aaaaaaaaga ctgggttctg ttctgtggag   24960
gttcttgtct taacatatcc actgttgatt gcccagatgt tgatgtaatt aatttagcag   25020
tcgtaaatag tttagcactt gcattaaata gaccaaaccc catagtaggt atttgaaata   25080
cagaataaat gtgaggtacc cctgctctaa aggagtttat agtccagagc tgacttatgg   25140
aggatttctt tctattattt ctgggtctgc tactaatttg tctatttcat atcctaatta   25200
tccttgtttt cattttgatt gaaagggga gagcatagaa attgtggtaa aaggtagttt   25260
tatttttat ttgagatgga gtcttgctct gtcacccagg ctggagtgca gtggcacaat   25320
ctcatctcat tgcaacctcc acctcccgcg ttcaagcaat tctcctgcct cagcctcccg   25380
agtagctggg attacaggtg tgcaccacca cgcccagcta attttgtat ttttagtaga   25440
gatggatttt accatgttgg ccagtctggt cttgaactcc cgacctcagg tgatcctctc   25500
actttggcct cccaaagtgt taggattaca ggcctcagcc actgcaccca gcctaaagtt   25560
agttttagat taagtgtttt catgttttcc cttgcaaagt aataaactgg tcaagttatc   25620
accttgttcc atctccatat taatcagggt ccaaacagga gatagaaacc atgcaacaat   25680
ttgagtagtt gaataaagaa ttataaacag gagattagag taataggga ttagatagta   25740
agaggtgaag agataggaac agcagatata aagaacaacc atttcctcct atggctgaga   25800
taccatcccc tcaccacact cccccaccta ctcactgaga tgcagacctt attgaagaga   25860
atgtaactgg cttgctgcga ggtaaagtca atgaggcgct ccccagtacc actctgaggg   25920
gatgctgggg aaaactgccc atgagaagag ggcacatgct gctggccact tgtgctaaag   25980
aacttgaagt ctgataggag tgcaccctaa cctggcatag aaacccttc ttcctgctga   26040
gtccctctag caccttatac tggcaaagct ttacattgca aacctccatt atcacagagc   26100
aagcaatgaa agatggactc agagctgagg cgataaattg atagctagca tagcctctaa   26160
actgactttt atgactacat tttatggata gaaagtgttc ttatatatat tgtttcttta   26220
cataatgggg gacttattca tggctgcaga tgagaaaaca gatcctaaga agttaagtga   26280
cttgcccaag gtcacacaaa gaattccact agttctaaaa tgacagtaat tacagttaac   26340
atacattgta tgtggcagat acatataaag cacatggcat taatttttt ttttgagatg   26400
gagtcttgct ctgtcgccaa gctggagtgc agtggcacga tctcggctta ctgcaacctc   26460
tgactccctg gttgaaggga ttctcctccc tcagcctccc gagtacctgg gattacaggc   26520
atgcgccacc acgcccagct aattttttgta ttttttagtag agacgtggtt tcatcatgtt   26580
ggccaggatg gtctcgatct cctgaccttg tgatccaccc gcctcggcct ccccaaatgc   26640
tgggattaca ggcgtgagcc accacgcccg gccacttggc atgaatttaa ttcccgccat   26700
aaacctgtga gataggtaat tctgttatat ccactttaca aatgaagaga ctgaggcaaa   26760
gaaagatgat gtaacttacg caaagctaca cagctcttaa gtagcagtgc caatatttga   26820
acacactcag actcgatcct gaggttttga ccactgtgtc atctggcctc aaatcttctg   26880
gccaccacat acaccatatg tgggcttttt ctccccctcc cactatctaa ggtaattgtt   26940
ctctcttatt ttcctgacag tttagaaatc agtccccaga atgtggatgt taatgtgcac   27000
cccacaaagc atgaagttca cttcctgcac gaggagagca tcctggagcg ggtgcagcag   27060
cacatcgaga gcaagctcct gggctccaat tcctccagga tgtacttcac ccaggtcagg   27120
gcgcttctca tccagctact tctctggggc ctttgaaatg tgcccggcca gacgtgagag   27180
cccagatttt tgcctgttat ttaggaactt tctttgcaag tattacctgg atagttttaa   27240
catttttcttc tttgaaccta gttataaagg tattgtgctg ttgttcctag cttagagtc   27300
```

```
ataaggcctg agctcacttc ctcactttgc ctccatctgg aaccttagac caacttccta   27360
ggaaaacgag ctgtctgaaa acagaatagg gtgcctcttc aatgtgctct tcactggaga   27420
tgttcaggag gaggctactc ccacctacac agggtgcagt ggagggtctg ggccccaggg   27480
aggcagcagg aagagtggaa agagcggagg ctctactgtt ggacagacct gggttaccag   27540
ccgtgtgact agccttccct ggcctccata tcccctcag taatgaagga atgtgtcatc    27600
cccaaatcca gggacagtta caagcagtca gtgaacagaa agtgtctggt acaggttcta   27660
agtgcttatt attctaagtc acttcactta cctgagttct cagttttcct atctataaga   27720
taagcaggtt ggataaaatg ttctccaata tactcctggt cctgagatga tgtgattgtg   27780
ggcagccctt taatcatggt gaagatgttc atcataagca cactgaaact acaaaatagg   27840
aatataaata ttttctccat taaattatgc tggatcctag aagcaaaaac tggaactgtg   27900
aaaccctact tcacagaaaa cttaaaattc ccaagcagat gaatgcttct cggaaggaca   27960
ctgacagtta cctacctgga aagaatctag atggaggtgg catgggcact aagcggtgag   28020
attaaaccca gttagggcag ccccaccagc cttggaaccc acacatctgg agattgttga   28080
tgcagagaga aaggttccta ctggtgagac ctgaaaggga tatgtggcag gtgggaggaa   28140
gaagttctgt ctggaaacca accttgttc ctccgttatt gattgactcc tggtaccaac    28200
atgagcccta ggtcttatag aggccataag tccctatgcc ttatagtgcc catggatgag   28260
atgaggccac acatgccccc agtgggttaa catgtctagc gtgggtaagg ctcttggagc   28320
actatgatac acaggaaatg cccagtaact cttagttggt ttgatatctg ttcccattgc   28380
tcacttaagc tcagtgcccc tttactgatc cttttattct gcctccctct gcacatgtgc   28440
attgagactc ctatctgaga cacacactgt gttgggtgcc cagggatgca gcatagatgt   28500
tgctgccttc cacagaagcg ctcatggtct gctagagaat atatcccatg ggagagaaaa   28560
acagactcgg gagaatatag caggggcccct tgtcctggac tttggcagtt aggaaaggga   28620
gggaagagac atggaggctg ggacccaaag gctaaatagg aatttgctgg gccaaagggg   28680
aggggaatg aaaagagtgt ttctggcaga ggaaatggca aggataaagg cctggaggcg    28740
caagagaata tgtgtttgag gatctgaaag ttgagtgcag tgggtccagt gttctctacc   28800
ctggctgcca ttagaattac ctgggaaact tttagaaaat tccagtgtct gggccctccc   28860
taaaacaata aatcattctt gggtggtggg gtctgggcat caggattgtt taaaccctc    28920
cccaggtact gtcatgtgca gctggggtta agctgtgctg gggtctgagt atggatctgt   28980
tagggcaagt ggcggtgatg gagttgaggc tgcagaattc aggccaaata gagaggtttt   29040
catcaggata ttaaagagtt tagatttcaa tttggtggga atggatggga tcttatttgc   29100
atttatgaa gagctccctg gttgcaatat cagaatggat tggagaggag caagatgaa    29160
gcctacagtg atttgggaga agtggtgagg gacttgagac acaggaagta gccccattca   29220
ctaatagttg agtatgtaga tttgctagga cctggaaatg gtttggctgg tggggagtgg   29280
gaagaaaggc ccaaagtgtg aaatgaagat ggagagcaca ttgcctagcc cagagtgatt   29340
gccatttgct ctgtcccagt tgaggtccaa ggggttggcc agagatcatg gagtctgtgg   29400
ctccatgggg agaagaacct ctcagcatgc ctccttgtct tatcctgggt tagtcagatt   29460
cattttgtta gattacattt ttttccagt ggaactctgc ttaagtcctg accagtatgt    29520
tttcagaagg atcagagggc ctgcccttgt ccattggtgc atgacaccag cttggtgggt   29580
tccttgctgc tccctgtttt catagggtta tcagaatacc ttctctccct gccaccagca   29640
```

```
ggtcacactg gctcctgact tttggccca tggaaccacc atctttctgc ttcttagatt    29700
gtgccttgta ctccactgat catggccagt acatcagaag ccctggtttg cagtgaatgc    29760
atttgatatg gaaatcagga accctgggga taccactcat catatttggt tgctgtgttt    29820
ttcctccaat cttcaccat aacaacaatc aactcaaaag atttctataa ccacttgtgt    29880 ggggtttct ccccacacac taaacaagca gtcagttcca gagtggacag cagctggtct    29940
cctccaattt aattccaaca ctgtctactt ggagatagca ttagatccca caggttgagg    30000
gtgcagtccc ctagactgcc cccagtctcc tgcttcagac accagtcaca agtccaggac    30060
tctagaagtt ctgaccagtt tcaagttggg gttcccacaa cccccactt tattttgat      30120 taatttgctg gagtggctca tagaactcag ggaaacactt agttttctgg acttattaca    30180
aagatttaaa aagataccaa taatagcca aataaagaga tatacagggc tagatctgga     30240
agggtctgga gcgcaggagc ttctgtcccc atctacttgg ctcccagcag atggatgagt    30300
tcttattcat tttcttgtca gcttcgacat gttcagctct ctggaagccc gcaaactctt    30360
gtcttcttgg gccttttatg gagacgtcgt taggcaggca tgattgaaac atggacaact    30420
gtgtcgaaat atgattggac ataaagggt ctaaactcag tgaggcctgt ttgttcagat    30480
tcttcttggc ctctctgtgg ccattctttc ctccaggata tgggggcagga cccctatgga    30540 atgagggtct tatgacccac aatcaaatta gagtcctgcc ttgggcaagt gaaggaaag     30600 caggagaagg taagagaaat tctgttgcct aagaccttct gaggcctaaa gcaccccaac    30660
attataacag aagacgataa caggactatg ggagttatga gctgggaacc ttggacaaaa    30720
atatatacat attaaataaa tattaagtgt atatatatac ttacgtatat taagtgtatg    30780
tgtgtgtgtg tatatatata ttttttaat ttactggttg gttttgggaa gcagaaatta     30840
ccataactac tcttaaaaat cttttaagtc tctttgaagt tagaaaagtc actgtacctt    30900 tttgttcca ttggccctgt acttcttatt ataccccagc aggaggagca taatgtgttg     30960
ttatatcatt ctggtgataa gattcataag tgggttcagc tggtgacagc ctgattccct    31020
cattgtaaac ttatccatca acatgtagct taatcgtttc accttttgtg atgaccatta    31080
cctgaatcag ttatttcatt agattgcaag attatgcttt tctgatttta tcatttcttc    31140
tgtattgact gtaattcttt ggtatagaag aactttccct tgttaatagc tatttggttg    31200
tcctgaagta cagttcttac tagaaagtaa gaccaaatgc tgaattatat ccctctagct    31260
atcaattttc gaaggaatga atggtgtcct agtaatttcc agtggtgttt aattacgttt    31320
tcccttctct ttctccttct cttattccct ccctctccat ctcctccctc ctcactttca    31380
gttttttgct ctttcagtat tttgtcatag ctgttaacag agcaacatat tttaatcaat    31440
tgtagtcatt tttcttttg gtgctcaaat tatcccgtct tagtcccatg gaagcaagcc     31500
cttggagcta gggccctcta ccttttgatg gatttccatt tgtcttgata atttccttgt    31560
ttctgacaag acaagatgtt gcaggcacat tttatacttt cccagcccaa accctggaat    31620
aggccttttc tccgaggagc tctagttcat tttagtggga aatggtattt agagactata    31680
atctgggatc tggagtcct cattgctact gagtagtcat tacttttagg cttttccagt     31740
ggtcagagct aggaaatatg tatatttaaa aatggacagt tgaatggttg ttgccaggag    31800
ctgggaggaa ggggaagtga gaaattgttt aatgggcaca gagtttcagt ttggggaaga    31860
tgaaaaagtt ctagagatag ctggtggtga tggttgcgca acaatgtaaa tgccactgag    31920
ctctcattta aaaatggtta aaatggtaaa ttttatatat attttaccac aataaaaaaa    31980
agtcttcttc tgggagcacc cccccaagac aaaaatatga aaattttaca ctgatacttc    32040
```

```
catttcaaga taattttaag attataagga ttttgcttaa ttcttgaatt ttatacctgt    32100
aaacctttta tacttcaaat ttcgggcaga attgcttcta taacaatgat aattataccct   32160 catactagct tctttcttag tactgctcca tttggggacc tgtatatcta tacttcttat    32220
tctgagtctc tccactatat atatatatat atatatatat tttttttttt tttttttttt    32280
aatacagact ttgctaccag gacttgctgg cccctctggg gagatggtta aatccacaac    32340
aagtctgacc tcgtcttcta cttctggaag tagtgataag gtctatgccc accagatgga    32400
tcgtacagat tcccgggaac agaagcttga tgcatttctg cagcctctga gcaaacccct    32460
gtccagtcag ccccaggcca ttgtcacaga ggataagaca gatatttcta gtggcagggc    32520
taggcagcaa gatgaggaga tgcttgaact cccagcccct gctgaagtgg ctgccaaaaa    32580
tcagagcttg gaggggggata caacaaaggg gacttcagaa atgtcagaga agagaggacc    32640
tacttccagc aaccccaggt atggcctttt gggaaaagta cagcctacct cctttattct    32700
gtaataaaac tgccttctaa ctttggcttt tcatgaatca cttgcatctt ctctctgcct    32760
gacttgccct ctggaatggt gctggaatgg tcctgtggcc ttgtccactg tctgcctttg    32820
accataactt gaaagtcacc caccatagtg tcctttgaaa taacttaaat gtccacagtt    32880
ccaagcatga gttaaaaaca cttcagaatg tagagtagtt gttcaattga ataaacacac    32940
acaccagaaa aaaagcaag tttatctttt atttttagta aagaattttg atagagcctc     33000
aacaccagaa atggctagag agagaagcct aacatatctg gaggattatt tttcatccta    33060
cttaaagctg ctttcactttt tttcaggaaa aaacacacgt tctgaatcta atttataaaa   33120
ctccctggcc gggtgctgtg gctcacacct ataatcccag cactttggga ggctgaggca    33180
ggtggatcac ctgaaatcaa gagttcaaga ccagcctgac caacatggtg aaaccccatc    33240
tctactaaaa atacaaaatt agccagacgt ggtggcgcat gcctgtaatc cccgctactc    33300
gggaggctga gacaggagaa tgacttgaac ccgggaggcg gaggttgcag tgagccgaga    33360
tcgcgccatt gcactccagc ctgggcaaca agagcgaaac tccgtctcaa aacaaacgaa    33420
caaacaaaaa ccccaaaaat ccctgaagta cgtgagctag tggtgaaaga aagctggaga    33480
aaaggagcag gaataataat aataataata ataataataa agattgtcat ttaattttga    33540
gtacttccag tgtacacttt gcaggtactc taagacatta cctcactgaa atctctaagg    33600
tagatattct ttatttaaag tgtacttgta tgaaacctgg agctcaaggt gaaggaattt    33660
gcccaaggct gcacttgcac tatcgtggca ctaattagcc gtgtgaactg ggacacgtta    33720
cttcagtttg ctcatttctg agtcagccta gcaagatgac ttctaagaat ttttttccagc  33780 cgggtacatt ggcctgtaat cccagcactt cgagaggcca aggtggaagg gtcacttgag    33840
tctaggagtt acacacaaca cacacacaca cacacacaca cacactagcc aggcatggtg    33900
gcaaatgcct gtagtctcag ctactccgga ggctcaggtg gaaggatcac ttgagcccag    33960
gaggttgggg ctgcagtgag ccatgatcac gccactgcac tccagcctgg ctgacagagt    34020
gagatcctct gtctcaaaaa aagaaaaaaa aaaagatttt tttccaggga ataataaagg    34080
aagctaatat ttatggagca tctacggtgt gccaaatact ttgcatacgt tatctcattt    34140
aatgctctta tccctgcagg gaaagtatta acatttgttt atcacttgca gaactaagtg    34200
atatttacca cagagtagac aaatattttc aagcccaaaa tcaagtggta tcactttttct   34260 gctgagaatg tttcagtggt ttcctttgct cttgggataa aacttaaatc cctcacccta    34320
cccttgctcc aaccctccac tttccttctc ccatgtggtg atttggccat acagctcttg    34380
```

```
tggctgatct gaactgactg agcttttttac ccttttgctc ttgctgttct tacagcctgg    34440
gaaccccctg gttacctctt ggcttggtgt ggtggcttac atctgtaatc ccagcactct    34500
gggaggccaa ggcggacgga tcacctgagg ttgggagtat gagaccagca agtcacctct    34560
tgccagtggc ctttgtccat tgagtctgaa gttctttctc ctctcatttc ccatcattc    34620 tattatgcta ccttgtttta ttttcttcat tgtgtttatt gatacttaaa atgatctctt    34680
ttctgttgct gtttgactct cccactagaa agtaagcatt gtagatcggg cactgtggct    34740
cacacctgta atcccagcac tttgtggggc agaggcgggt ggatcacctg aggtcaggag    34800
ttcgagacca gcctggccaa cacggtgaaa ccccatctct actaaaaata caaaaaatag    34860
ctgggtatgg tggctcgtac ctgtaatccc agctactcag gaggctgaga catgagactc    34920
acttgaacct gggaggcaga ggctgcagtg agctgagatc acaccacagc actccagcct    34980
ggaagacata gtgagactct ctctcaaaaa aaaaaaaaaa aaaaaggaa gtaagcattg    35040 tgagggcagg taccttctct gttttgttca ttgctggatg tagttagtat acagcagtat    35100
ctgatggatg gatagatgga ggaatgaatg aatgagactt cacaaattca gctcacttgc    35160
tcaaggccct gcagctctac gggatgaagc tatactccag agtcctgcta cattggctgt    35220
gtggccagct gctgggatct gagggttgtc agataagcag tctaccagag aacagactga    35280
tcttgttggc cttctgccag cacagggggtt cattcacagc tctgtagaac cagcacagag    35340
aagttgcttg ctcctccaaa atgcaaccca caaaatttgg ctaagtttaa aaacaagaat    35400
aataatgatc tgcacttcct tttcttcatt gcagaaagag acatcgggaa gattctgatg    35460
tggaaatggt ggaagatgat tcccgaaagg aaatgactgc agcttgtacc ccccggagaa    35520
ggatcattaa cctcactagt gttttgagtc tccaggaaga aattaatgag cagggacatg    35580
agggtacgta aacgctgtgg cctgcctggg atgcataggg cctcaactgc caaggttttg    35640
gaaatggaga aagcagtcat gttgtcagag tggccactac agttttgctg gcaagctcc    35700 tcttccttta ctaacccaca atagcatcag cttaaagaca atttttgatt gggagaaaag    35760
ggagaaaaat aatctctgtt tatttttaatt agcattaatt ggtattcttg ttaaaccata    35820
ggagtcagag taaatcagcc atttcaccaa ttttcagttt gtttctgtct tagctaacag    35880
cagtgtaatg gtcagcaaaa ttcttatctt gtgtactgaa tggcatgtcc tgttgctgaa    35940
agtgcacagg cttgggaggt agccatgagc tcaaatcctg gcactaccac ctctcttgtg    36000
tgaccttaga ctcctgacct ttctatgcct cagttctttc ttacctataa aatgaaatta    36060
attttaccct taaagatcat cgtgctgatt agagataaaa tataaataat aacacttgtt    36120
acagagcaag gagttgacac ttttatattc tgaagacaaa gtggtaaatc attatcatct    36180
atgtcagaaa tagcttttga gaatacctga gtatagaact atcttgatcc ctgttacttc    36240
aaaactaaaa taatggtttt aggaattaaa aggtgaggct agtcacctcc aagggatgaa    36300
ctgactcagg gattgaggta tataacagtg aactggtcca acaacagtc ctgaccccac    36360 tttatgagtg agactatgag taatggtcta agtgtagaca tcattgtcca gggctccagt    36420
aggcagctct gtacttgaga atttagcagt gaccttctta tttttcatct attataccctt    36480 tttttttttt tttttttgac acagggtctc actttgtcac ccagctggag tgtggtggtg    36540
caatcatggc ccactgcagc ctcaacctcc ctgggcttag gtgatcctcc cacctcagct    36600
tcctgagtag ctgtaattac aggcatgtgc catcatgccc agctaatttt tcttttctta    36660
gaggtggggt tttgccatgt ttcccaggct ggtcttgaac tcctaggctc tcacctctgt    36720
cttccaaagt gctgggatta caggtgtgag ccaccacacc tggcctatta cacatttctt    36780
```

```
aattaaagta gtcaaatttg aaaactgtta caaagtgtat cttaaaatac gacgatctgg   36840
tttaattttt aaaagatatg agtagccaag gagcaattct gtgcctttcc cactagtccc   36900 taaccttta aagcagctgc ttcttggctg ggctcagtgg ttcacccctg taatcccagc    36960
actttgggag gccaaggcgg gtggatcatg agtcgagatc atcctggcta acacagtgaa   37020
accctgtctc tactaaaaat agaaaaaaat agctgggcgg ggtggcggat gcctatagtc   37080
ccagctactc gggaggctga ggcaggagaa tggcatgaac acgggaggca gaggttgcag   37140
tgagtcgaga ttgtggcact gcactccagc ctgggcgaca gagcgagact ccatctcaaa   37200
aggaaaaaaa aaaaaaaaac ccatctgctt ttgattcagt ggcttcttta attttgtcgg   37260
tctcagtcac catttgtcta agcaaattca ggcaggcttc accttgcctt tctacatttg   37320 ttccctttc ttagcatttt gggcctttgt ttacacgtgg gaaaagaccc acaggtcgtc    37380 tctcccttg ggcaggatac aggcttcctg tgactgaggt tttgctagct gtagaagtgg    37440
ctgccaattg gcttctggtt tttatttcca tgatttgctc cagtggctct tcccttccat   37500
cattgttagc tttcaagcta ggaactttta aaatgctttt aaataaaagt gagctgttac   37560
ttgatgcatt tagcagtctt cctcacagtg gttttgatag acagactccc tcagtttgga   37620
atttatgagt tttctttaag ggtttgtctc cctcatgtat agcaggctgt tgaaagttac   37680
aatgtcaata actttctgaa tagtatcaaa ctgttttcag tgcagtgtat taacaaaact   37740
aacctgcctc aagtttggtc agctttggag tcttactgag gctaaaatga taaatctaaa   37800
tgatttaaaa ttgtgtattc ctacacagta tctcacttaa ttatgtaata gtcttgtgag   37860
tgaggcagag cagatgccgt tttctctatt ttaaagatga ggaaaatgga atggaaaatg   37920
gaaaggacag actaattgca acatcctcgc aatcaaaaac aggcccaggt tcatgccttg   37980
ttggcagtgg gttgctactg gctgtggcct tcatgcagga aggctagatg cataaccagg   38040
tcaacagccc gtgcaggaca agcacgccat gtaattctga ttccatcgac tgaggctggt   38100
gttttcaaac gtgctggtgt agggtcttac agacagagtc atctgtgcta tggggaatgg   38160
aatgtgctct tgcttggag ccagaactcc tctgaagctc ccaccaccta caccattcag    38220
aggccagaca gaaatttgtt caccattttg ggcatgattt tcgtgctttt gtaaaatgtg   38280
cttcactgca gcccttactg ggctgtggtg atgaacactt aagatactgt gtgtgtgctt   38340
tataatctgt aaggcactgt tcaaggggag ggacctctgc catgagcccc tacccactgg   38400
tatctggttg acatccaaag ccccagcctg ggagaagctg attctctagt tgaatgctgt   38460
atagggattt gactgaggct cagatttggt gaggaagacc actaaccta acagaccaac     38520 aggctggcta ctccctgatg aagttcccca ggccatgaaa gaagtaagag atacattcct   38580
tgtaacagct ttcttagttg cacctgtatg attatttgat cagtgtgttg tctgtgcagg   38640
gatcatgtct gtggagctca ccacctcgtc ctcggtgctg agcagagtgc ctggcatgtg   38700
tactcagtag atatttgcta agggagcgag tcagtgattg agaggagcag cctgggaggt   38760
aaagccctag aatctttatt ttaaagggat atcaaagttg aacattcagt tagacagttc   38820
tcttgagtcc agggatttac ccatccatgg tggacacact ttcagttaaa aagtaaggtt   38880
aattttgaca ggttgcagta tccaggcaag cattctatgg aataaggctc atctcaggga   38940
ttagtaatga ctgaattaac ttactgctag tcccataatt ttgacgttaa ttaatggggt   39000 taagaaaatgt cataagctat ttggtaccat ttaaagtgaa aatacccttta acgtttttg   39060 cctccagata tccacactta atttcatttt cttgctcttt ggtgaacagt cctgggtctg   39120
```

```
aatgtatata tccatggttt gtcactaggt gacaggtttt tttggaacaa gaaatcagtt    39180
cagtgaacat ttgtcaagta tcttctctgt aaaaagtgta atgtgccaag ctcagaagta    39240
ggaagtgaaa tggataaact atgacccctg ccttaaagaa caccatggtg ttgtatggga    39300
attgtttagg tagaatgaaa gaaatcctct aatagagata tgaggccagt tcagcagaaa    39360
gccagggtga gatctcctga gagggatgga agggtgtctt gatcatctct ggtagcagca    39420
aaggcactgg catacagtgg ccactggaag acaaccagca ggggatgggg gcgtttaccc    39480
ttgcaagtga gcattaggaa ctagaggact gattgcccct tcttcagctt tggtttccct    39540
tgctgcagaa aaagatgctg agactcatgg cctcggttat gaactcagat atgtggtttg    39600
gctttgaagc acagatggat tttgtccgat tttggcaggg aaatgcctac agacagcact    39660
atgggcatat ttaggttagg gacgaaatgc aagttgatta agtcctgata agaggctgtg    39720
aagaggtcca agaagcctca caatgcccaa tgaagaaaag ccctgtgctt ggtgctgccg    39780
cctcccttcc ccgtcctgct ggcagggctg cgcttcagta gctctggatg cgtcagagca    39840
gtccatgaac attctgtgtg gaaatctctc gactgtttta gtggattaca ctgctctccc    39900
tttcctccag tgcctcgtta ttcagtatta tttgatgttc tccagctttt aaaataatca    39960
ttttccgcct acgcagaaca tcctgtagag acgttgaggt tccagtggga acagagagga    40020
atacttattc taaaaatgaa gaaataaaac cttttttttat ggagtgggtg atagtattgc    40080
agaacttcta taatagtatg agaattcact tgtggtgcca aagcttaaaa aaaaagtata    40140
gtaaaaacat aatgtatagg cttattgctg tgctatgacc catgccccgt tttctccaac    40200
ctctcttgtc ctcactcttc cttttgctg gtgatatttt tacttatttc atgaaaaaaa    40260
agataacata tacacacaca tagatatatg cacaagtata tgtatatatg tgtgcataac    40320
acacataaac atatacattg gtaaatttaa aaacatattt atgaaatata tgtagcatct    40380
acagaaaaac atgaacactt gtgagaatag catctgccta aaaaatagga catcaccatc    40440
acctttgagg ctcttatgtg ctgctcccct gtgccattcc cttcccttct tccttagagg    40500
tgattactat tctaaatttt gggattatta tttcctttt ttattatagt gttttaatta    40560
cagttttatt acctgtattt gtattcctaa aaatttgttt acttttgcaa gctttagatt    40620 ttataaagt agaattacac tgtaagttta atttttctgt aatttatata tagctacaca    40680
tatattccta agattcatcc atcttgttac atatagctct ggtttacctt ttctgtataa    40740
tatagattct gcttcgtgaa tttacagttc attcattctt ctgttaaagg acagttggag    40800
gactcatatg gcctcagtct ctgtgtcccc acatgccacc ctgcttccca gcctcatatg    40860
agttgattgg tggcctggca tactggatga gaagctctag gtcatatatt aagagagtt    40920 attgctgggt cataaaatga cagattgttt tccagagggg tcatattgat ttaaattatc    40980
accaacaatt atattgtcag attttttacca gtttggtgat tgtgaaacag tgtctgatgg    41040 tagttttat ttgcattttc ttggttgaaa taaagttgtg tatttcagcc aggtgcgttg    41100
gctcatgcct ataatcccag cactttagga ggccaaggtg gcagatcac ttgaggccag    41160 gagttcaaga ccagcccagc caacgtggca aaacccatc tctactaaaa atacaaaaat    41220
tagatgggta tggtgtcaca tgcctgtaat cccagctact caggaggctg aggcacaaga    41280
cttacttgaa cccgggagat agatgttgca gtgagccgag attgtaccac tgcactccag    41340
cctgggcaac agagcaataa ctaaataaat aagtaatcaa ttaataaata agtatatttc    41400
ctcagctgtt aagtacctgt tcaagttttt tacccaatat ttgatgggct cttttttgt    41460 cttttctaat taattttgg agttttgat atattctaga tagtaatgag ttacatgaaa    41520
```

```
atatccctag ttagggatc ctctagtaac ttttaaat gaatacttgt tttaggaaca    41580
gaaattctta gatttaatgt aggcagattt tatcaattgt tctttacaga ttggctttgt   41640
agcttaagaa atccttccta actttgcaat aattaaagat atgctcttag attgtttcct   41700
aaaagactga tacttaagcc tctagcccac ctggaattga ttttcacaga tactacattt   41760
tttactagtt atagattggc cccttcgtag agcaagtccg atagctgcca tttttatggc   41820
agcatgtgct cacttagtgt ctctgtcaaa ttttggtaat tctcacaata tttccaactt   41880
tttcattatt actatatctg ttatggtgat ctgtgatcac tgatctttgg cattactatt   41940
gtaattgttt ggggcaccat taagctcact gtcttatgtg ggcataaacc atgcccacat   42000
aagacagtga gcttaattaa taaatgtgtg tgctcagacc cctccactga ctgggtgttc   42060
acatgtcttc cttactctcc tcaggcctcc ttattccttg agacgcaata atatggaaac   42120
taggcaaatt aataacccca cagcgtccac aagtgtttaa gtgaaaggaa gaggctgggc   42180
gcaatggctc acatttgagc tcacaaatga gcccatgctc atttgccatt ccaaaaatcc   42240
cagggccctt aagaattatg ctaactctac tctgcctctg ctctataaat ggaacaacaa   42300
agcctagatg acagcacatc tttttagaac atgatttact gaatatttta agcccattgt   42360
ggagacctac tgctcagaaa aaaagattcc tttcaaaagc ctgtaatccc agcactttgg   42420
gaggccaatg caggtcgatc acctgaggtc aagagttcga gaccagcctg ccaacatgg    42480 tgaaacacgt ctttattaaa aatacaaaaa ttagccaggc ctggtggtag atgcctgtag   42540
tcctggctat tcaggaggct gaggcatgag aatcacctga acccaggagg tggaggttgc   42600
agtgagccga tatcatgcca ttgcactcca gcctgggcac cagagtgaga ctacgtctca   42660
aaaacaaaac aaaaaaaaaa aactgaaagg aagagcttaa tgagaaaggc atattaaaag   42720
ccagtatagg ttgaaagcta ggcctcttgt gcaagttagc caagttatac atgaatggta   42780
aagcaaaaca gctttattgc tgtaataaag aaagttttag tggtctggat agaagatcaa   42840
atcagtcaca gcattcccttt aagccaaagc ctaatccagg gtaaagcccct aacttgcttc   42900 aattctttga agactgagag gggtgaggaa gctacagaag aaaacttgga agccagcaga   42960
gattgatgag gtttaaggga agaagccaca agtgctgatg tagaagctgt agcaagttat   43020
ccaaaagatc taattgatga aggtggctta cactaaacaa cagattttca atgtagacaa   43080
aacaatcttc tattagaagg tgtcatctat gacttacata gttaaagagg aaaagtcact   43140
gcctggcttc aaagcttcaa aagacaggtt gactctaata ggtactaatg catctggtga   43200
ctttaagttg aagccagtgc tcatttgcta ttccaaaaat cccagggccc ttaagaatta   43260
tgctaactct actctgcctg tgctctataa atggaacaac aaagcctaga tgacagcatc   43320
tttttagaac atgatttact gaatatttta agcccattgt tgagacctac tgttcagaaa   43380
aaaagattcc tttcaaaata ttactgctca ttaacaatgt acctggccac cctagatctg   43440
taatggagat atataaggac atgaacacta acacagcatc cattctgcaa cccatggatc   43500
aaggagtgat actgactttc aagtcttatt taagaaatac atttcatagg gctctagctg   43560
ccatagatag tgattcttct gatggatctg agccaagtaa attgaaaacc tctggaaaga   43620
attcatcatt ttagatgtcc tgagaaacat tcgagattcc tgggaagaag tcaaaatatc   43680
aacattaaca ggagtttgga agaaattgca tccagccctc atggataact ttgaggggtt   43740
caagacttca gtggaggaag tagctgcaga tgtggtggaa atcacaagaa aattagaatt   43800
agaagtggag cctgaggata tgactgaatt gctgcaatcc catgataaaa tttgaacaga   43860
```

```
tgaggagttg cttcttatgg atgagcatag aaagtagttt cttgagaaag aacttaattc   43920
tggtgaagat gctgttaata ttgttgaaat ggcaacaaag gatttagaat attatataaa   43980
cttggtaaag cagcagcagg gtttgagtgg attgacacta gttttggaag aatttctact   44040
gtgagtaaaa tgctatcaaa caacatgaca agctacagag aaatctttca tgaaaggaaa   44100
aatcaattga tgcagcaaac ttcactgttg tcttatttca agaaattgca acagcttcct   44160
cagccttcag caatcaccac cctgatcagt caacagccat catcagggct agatcctcca   44220
ccagcaaaaa gataacaatt cgccgacagc tcagatgact gttaccattt tttagcaaaa   44280
acctttttaa ttttatttat ttatttattg gagacagaga ttcactctgt cgcccaggct   44340
ggagtgcagt ggcacaatct cagctcactg caaccaccac ctcccaggtt caagtgactc   44400
ttgtgcctca gcctcccaag tagctgggat tataagcatg tgccaccacg cctggccaat   44460
ttttgtattt ttagtagagg caggatttta ctatgttggc caggcttgtc tcgaactcat   44520
gatctctggt gatctgccca cctcgggttc ccaaagtgct ggtattattg gcatgagcca   44580
ctgcgcccgg ccagcaaaaa agtgttttta aattaagcta cctacgttga ttttagacat   44640
aatgctattt gcacacttaa tagattacag tgtggtgtaa acataagttt tatatgcact   44700
gaaaaacaaa aaatttcaca tgacttgctt tattgtgata ttgactttat tcctgtagtc   44760
tggaactgaa cctgcaatat ctcagaggta tgcctgtatc tacttgttct gtgatacttg   44820
ttattgtcag tttgttttgga tttaccacat attatttgat cataattctt tcctgtagat   44880
gttttatggt ctgcctaaac ctttagtggg gcctttgatg gcttagtcct ttcaggctta   44940
agacaataga agtttatttc tcagagttct aaaagctggg aagtccaaga tcaaggcacc   45000
gacagattta gtgtctagtg aaggcccgct tcctcataca tggcaccttc tagctgtatc   45060
cttacatagt ggaagggaat agctagctct ctggagtttc tttcataagg gctaatccca   45120
ctaatcccaa ttatgaggga agacctaatc acctcccaaa ggccccacct cctaatagta   45180
tcaccttggg ggttaggatt taacatatga attttgtggg gacacagaca ttcaaacaat   45240
agccatggca aacttttttg ctttgtctaa ttcactctta ttttgaaaag tatttgtgtt   45300
gggtttaaaa ctccagattg gtaattattt tttcttagtg cattgaaggt aatagtgtat   45360 catttctga tttctactct tgctcttgaa aattcagcta tcaatcttaa aatttattac   45420
ctgttgaaaa tccagctacc agtcttatat tttatttact tagtgggtaa tctctcttct   45480
gagtaccttt aagatctcct ttcagaaata ccatgtagta accctgtgtg tcacgtgtgg   45540
attttgttgg gcttgctagc tgagacttga cagttttcat cacttctggg atattctcag   45600
gtattttgtc ttcaaagtct tcagatattg tcctcttcct gccctctctc cgactccttc   45660
tggaacatga gttatgtatt tattatctcc catgtgcata agttatcttt acatattttc   45720
aatttcttta tctttctgtg ctacattctg gataattttg ttgatctacc ttccagttaa   45780
ttagcttgtt aactttgtca aatctctttt taagtctatc ttgatttttc ttttcaatta   45840
ttgtattttt cattttttaaa aactttatgt gctcttttgg aaatcttgat cccaggagat   45900
agtggatagt gtcctgctgc ttactcatgg ttttaatagt tcttgagcat gctgaacata   45960 cttatttat gttatttgct aatctttcca attcctgaaa cctttacaga tctcattctg   46020
tggattcttc tggattctaa ttcatggggc attttttttg tttttttgtta attcctcata   46080 ctttatctgt ggggaattac ttgaagcctg ggttgacaat gaaattctgc agagagaatt   46140
tgcatttgat tctactggag gaacagtcag ccccgatatc agtttaaatt aaaatctctg   46200
cttaaggttt tcaggcaacc tgcttagcat gaatcctggc tggaaaagca tgtgaggacc   46260
```

```
agtttatgat tacacattca cagggtgtca tgttttcttc caacaccaat gctagaggtg    46320
gcagttttgc ttactgccct tggagggaca ggggagtggg catgggcata gtagtatggt    46380
tttccttttc actggggtg cagcccttgg agtctcagct taatgtgttg gggaagtggt    46440
ctcctattag actctccatt tcaaaccatt ccatgatttt gtcctccttt tgccaccttc    46500
cgagcctgta aaaactaatg tttgtgattc ctgaggtttc tctaatgtct tttaataaag    46560
ttgacctcag agatctcgtt acctctctga gttcctgctt tgtcttagat tttgatcctt    46620
gagtgttctt taatctttta gcaattcctt gttgcatgtt aaaagattag ttatatttta    46680
ttcctcattt gtgttcgttt tcaccaggag gctcaattca ggcttctttg cttacttggt    46740
gtctctagtt ctggtgcctg gtgctttggt caatgaagtg gggttggtag gattctatta    46800
cttacctgtt ttttggtttt atttttgtt ttgcagttct ccgggagatg ttgcataacc    46860
actccttcgt gggctgtgtg aatcctcagt gggccttggc acagcatcaa accaagttat    46920
accttctcaa caccaccaag cttaggtaaa tcagctgagt gtgtgaacaa gcagagctac    46980
tacaacaatg gtccagggag cacaggcaca aaagctaagg agagcagcat gaggtagttg    47040
ggagggcaca ggctttggag tcagacacat gtggtttcaa atccaagttc gaccatttcc    47100
catttatttg actgtagaca agttacattc ctaaactatg tctcagattt ctcatctgta    47160
agttgtggta ttactagtta acatgcaggg gttttgtttg tttgtttgtt tgtttgtttg    47220
tgagggtaag aaataaccca agaagcctag tccttggtag ttgctcagtg ccctataaat    47280
gttgtgaacc aggtggtgag ggtttggtgc tgctagagaa ttctggtatc tgctctgtgc    47340
aacagagtac tgtaggtgat gcaagagaaa gaagacctga tgccttcttt cctcccagct    47400
ttgagaatgg agcaaaggcc tacccccagcc accaagtgag ccagtgggct tgatcagcac    47460
aggaaaggtg accccggcag tttcatttga ctattgcatg gctggcaaca tttctattga    47520
ttgtttccag ggaccttggc ggatgagctc ctgttgagtc tagcatctct gttaaatctg    47580
ttctcaaata ggtaatgcat atgggaggat gctgccacct tgcatctact agacatcacc    47640
tatctactgt gagactctcc ctctaagccc tgctgtggcc tcagagtgct tattggccct    47700
gtgagtgggg cagccactat acattgcatg gagttggtac atgagataga aacctattcg    47760
ccatcccttg aaactgcccc agtccagaag cttcctgtta gcacatgtac ctccttgtat    47820
gtattcagaa ctcattccat ttaggcttgg aaacccgttt ggtgcaactc tgttcaagtt    47880
ccattgtctg ctttgagaat gcttgggctt gtatagtgag ctgtcacttt ttaatttgtt    47940
aggaattcta ctcgccttgc ttttttctttt ccagcatgtt taagggaatg acctccaagg    48000
ccccaaatca cagttgtatt catgttcttt catttcacag atacaatcca ggccagtccc    48060
agatttgcag ctgttaataa atgtgaatgg ttttccagta aggggtaga aaaacatagg    48120 gagagaaccg ggttcagagt tcaatatctg gattcaagtc cttcctttag cactttacta    48180
actgatgtag aataagtcag ctactcaata ggtgcctcag tttccccacc aaaatgcaga    48240
catagaaggt gctttgtctg ctttgatgag aagtctttaa gcaagtctat ggggttcaat    48300
gtgttttaag aactataaag taccatataa atgtggcctt tattcccatt gtgttcttgg    48360
aagtaattca atatagtgtg tacttcatag ctgcttttgg actattgcca gccagtgtat    48420
catcctaaac tacatgtcag catagtataa tcctgcctta ggtctacttt tgattattta    48480
ggaagactcc ctgcccttcc tatacatttc acataatttt taataagttg taaaaaagtg    48540
atttatagga ttcttttgtaa gtgggggaag ttaagcagac aaaaagtttt taaatcttac    48600
```

-continued

```
tgcagagtgt caggaacctt ttatagcacc agacaggtag ggacagaaca tgagtggcag    48660
caagccagac ttggtcttag tgctctaacc tgtctgttag aggctggcca gtcagacccc    48720
tggttgaaga cgttgggaat cccagctctt tggaggggta agagattttg ttagactgtt    48780
aaccagattc cacagccagg cagaactatt tctgtctcat ccatgtttca gggattactt    48840
ctcccatttt gtcccaactg gttgtatctc aagcatgaat tcagcttttc cttaaagtca    48900 cttcatttt atttt cagtg aagaactgtt ctaccagata ctcatttatg attttgccaa    48960
ttttggtgtt ctcaggttat cggtaagttt agatcctttt cacttctgaa atttcaactg    49020
atcgtttctg aaaatagtag ctctccacta atatcttatt tgtagtatgt taaattttc    49080 taaaacttct aaggatagtt gctgtattgt atgatttgca tatggaggta tctataagaa    49140
gttttatact ttttagcaaa atagtcattt ggtagccaac ttaaacaaat gtttattaat    49200
atagaagtta ataatatcta ctgatactcg gccgggtgcg gtggctcatg cctgtaatcc    49260
caccactttg ggaggctgag gcgggcagat catttgaggt caggagttca agaccagcct    49320
gaccaatatg atgaaaccct gtctctacta aattacaaaa attagcaggg tatggtggtg    49380
ggcgcctgta atcccagcta ctcaggaggc taaggcagga gaatcatttg aacccaggag    49440
gcagaggttg caatgagctg agatcacgcc actgcactcc agcctgggca acagagcaag    49500
attccctcaa aaaataaat atctactgac acttaatact tggaaaggga taaaataaa    49560 cattgtctaa agccgtggtc caaacacaac ccctgccaac aatttagtc catttcttcc    49620 aagactttt ttttctatg cctttgtga aaactgtcaa aaactttttc aatgctgaat    49680
tttagttctg agttaaaaat catactacct gtttatatgg tttcatatcc acttttttca    49740
tgtgatatac tctacaaaaa gcctgctgag attttgattg ggattatgtt gaatctagat    49800
caatttaggg tgaaaacttt tgttagata aatcccttag tatttcacat ttttaaatgc    49860
taaatggcat ttttcaaaaa ttttcttttt tctttttcttt tttgagacag agtcttgctc    49920
tgttgcccag gctggagtgc aatggcaaaa tcttggttca ctgcaacctc cgcctcctgg    49980
gttcaagcga ttctcaaact gcctcagcct cccaagtagc tgggattaca ggcatgtgcc    50040
accatgcccg gctaattttt taaactattt atagtagaga gggggtttca ccatgttggc    50100
caggctggtc ttgaactcct gacctcaggt gatctgccca ccttggcttc ccaaagtgct    50160
gggattacag gtgtgagcca ctgcacctgg cctcaaattt ttttttttt tttttttaag    50220 agacagggt ctcactcttg cctaggctgg agtgcagtgg cgtgatcata ggtcactgaa    50280
gctttgaact cctaggctca agtagctagg aatacaagtg tgtaccacta cacctggcta    50340 attttttaa aaaattttt ttcgtagaaa cgggagtctt gtgttaccaa ggctaatctc    50400
aaactcatgg cctcaagtga tactcttgcc tcagcctccc agagtgctag gattgtaggc    50460
atgagttact tcacccagcc aaaaaacttc aatttcctat tgtttatttg ctagtatata    50520
gaaatacata tagttttgta ccttgatgct gtatcttgca accttgttaa actcacttac    50580
tagttctagt atatttttg tagattctat cagattttct atatatgtat catgtcttct    50640
gagaataaag aaacttttac ttcttgctgt gcaaactgaa cacctttct ttctttcttt    50700 ctttttttaa gacggagttt tgctcttgtc acccaggctg gagtgcagtg gctgatctc    50760 ggcttactgc aacctccacc tcctgggttc aggcaattct cctgcctcag cctcctgagt    50820
agctgggatt acaggcgctc gccaccacgc ccggctaatt ttttgtatt tttagtagag    50880 atggggtttc accatgtggc cgagctggtc ttgaactcct gacctcaggt aatctgcttg    50940
tctcggcctc ccaaagtgct gggattacag gcgtgaatta ctgcgcccgg ctgcctttta    51000
```

```
tttctttctc ttgactgact gcactggcta gagcctccaa tacaatgttg aatagaagtg    51060
gtaagaatgg gccaggcatg gtggctcatg cctctaatcc tagcactttg ggagagtatg    51120
gtgggcaggt tacttgaggc caggagtttg agatcagcct ggcgaacatg gtgaaactct    51180
gtctctatta aaatacaaa atatagttgg gtgtggcagt tcacgtctgt aatcccagct    51240
acttgggtgg ctgaggcatg agaatcactt gaacccagga ggcggaggtt gcagtgagcc    51300
aagaatgcac cactgcactc cagcctgggc aacacacaca cacacgaaaa acgaagtggt    51360
aaggatggaa atccttctct tcttcctgat ctaaggggga aagggggaaag ttacaaaaca    51420
ttcagtatgc tgttagccat ataggttttt ttgtagatgc ccattatgag gttgaggaag    51480
ttccctctgt tccttatttg ctacagattt tatttaggat tggatgttga attttttttca    51540
aatgcttttt ttgcatctac tgagataatc atatgatttt tcttttatag tttgttaata    51600
tagtgaatta cattgatttt cttatgttaa accaatcttt gcattcctgg gatgaactct    51660
gcttggttat aatatataat ccttttatt tattatggga tttgatttgc taaaatttt    51720
attataatta ttttatctgt gctcatgatt gttactagtt tatagttttc ttttagtctt    51780
tggtttttgt atcagggtaa tgctggcctc atagaatgag ttggtaagta tccctcctt    51840
ttccattttc tgaaagagtt ttgtgtagaa ttgatgttaa aattattgct taatgtttgg    51900
cagaactcaa cagtgaagcc atctgggctt ggagattttc ttcatgggaa ggttttaac    51960
tgcaaattct atttctttaa tagtatagag ctattcaggt tatctgtttc ttcttaggta    52020
agctttggta ttttgtttct ttgaagaaat ttgtcgcatt taatctaaat ttttaaattt    52080
actgacataa agttatttat aatatttctt attcttttat tatctatgga tctcttggtg    52140
acataacctc tctcattcct aatattggta atttcaggct tttctttta acttggtcag    52200
tctggctaga ggtttatcaa ttttattgat cttctcaaag aactaacttt tggtttcata    52260
gatttttcta ttttctattt cattgatatc tgctctgact tttaatcttt cttataccta    52320
ttttggttta atttgtcttc tgtttcacat ttcttttttt tttttttttt tttttttga    52380
gacagagtct tgctctgtcg cccaggctgg agtgcagtac agtggtgcga tcttggctca    52440
ctgtaacctc agccttccag gttcaagcga ttcctgtttc taagcctccc aagtagctga    52500
gattacaggc atgcaccacc agctaatttt tgtatttta gtagagatgg ggtttcactg    52560
tgttggccag gctggtctca aactcctgac ctcaggtgat ccacctgcct tggcctccca    52620
gagtgctggg attacaggtg tgagccactg tggctggcct gtttcacatt tcttaaggta    52680
gaagctgagg tcacggattt gagacctttc ttctttcta atacaggtgt taagtgctac    52740
aaatatccct taagcactgc ttcaacagca tcccacaaat tttgatagtt tgttttcatt    52800
ttcattcagt tcaaaatacc ttctaatttc ccttttgatt tcgtctttga cctacaggtt    52860
ttttagaact gtgttattta gtttccaatc tcttgaggat ttttaaaaca atatgttatt    52920
gatttctaat ttatttccat ctcagtcaaa gaacatactt gccttttttt atacatttat    52980
tgaaactttt tttatggccc agaatatggt ctgtgttggt aaatgttcca tgtgtacttg    53040
aaaataattt gtattctgat ctcattgagt tgaatgttct aggtatatca agttgatagt    53100
gatgcccaag tctcctgtat ctttactgat tttctgcctg ttctgttatt gagaaagggg    53160
tattgaaact tccaactata attatgattt gtctgttctc tttgcagttc tcttagtttt    53220
tgccttcata tatatataca tatatatgta tatatatata tatttttttt tttttgagat    53280
ggagtcttgc tctgttgccc aggctggagt gcagtggtgt gatcttggct cactgcaagc    53340
```

-continued

| | | | | | |
|---|---|---|---|---|---|
| tccgcctccc | aggttcacgc | cattctcctg | cctcagcctc | ccgaatagct | gggactacag | 53400 |
| gcgcccacca | ccacgcccag | ctaatttttt | gtattttag | tagagacagg | gtttcaccat | 53460 |
| gttagcaagg | atggtctcga | tctgacctcg | tgatccgccc | agcttagcct | cccaaagtgc | 53520 |
| tgggattaca | ggcatgagcc | actgcaccca | gcccatatat | tttaaagctc | tgttattggg | 53580 |
| tacataaaca | tttaggattg | ttatatcctt | ttgataatgg | actcttctat | tatgaaaaga | 53640 |
| taatatactg | tgggtttata | acatatgtaa | aagtatgagt | aacatattat | cagaagggga | 53700 |
| gaaatggaag | ataacttagg | catcttattt | ttaagcatag | ttttcccttt | gtttctgcat | 53760 |
| tagatgattt | acctgaaatg | tcattcaatt | taacttactc | tccatcctca | cccgcccagc | 53820 |
| tttggttatg | aggcagtaga | agaaatgat | ctgcctgtgg | ttttctagaa | atacgaaagt | 53880 |
| tgagtcctta | aggctacaca | gaaagaaagt | acctccccag | ggcttcaccc | ttcccatcct | 53940 |
| ttcagcaggc | tttttgtctg | tcgtatcttc | tctgttgaaa | tggccattga | caagaggagg | 54000 |
| aaagggttt | tgttgtggat | tgttcaggca | cttcctttgg | ggtatatggg | ggatgagtgt | 54060 |
| tacatttatg | gtttctcacc | tgccattctg | atagtggatt | cttgggaatt | caggcttcat | 54120 |
| ttggatgctc | cgttaaagct | tgctccttca | tgttcttgct | tcttcctagg | agccagcacc | 54180 |
| gctctttgac | cttgccatgc | ttgccttaga | tagtccagag | agtggctgga | cagaggaaga | 54240 |
| tggtcccaaa | gaaggacttg | ctgaatacat | tgttgagttt | ctgaagaaga | aggctgagat | 54300 |
| gcttgcagac | tatttctctt | tggaaattga | tgaggtgtga | cagccattct | tatacttctg | 54360 |
| ttgtattctt | caaataaaat | ttccagccgg | gtgcggtggc | tcatggctgt | aatcccagca | 54420 |
| ctttgggagg | ctgaggtggg | cagataactt | ggggtcagga | gttcaaaacc | agctggccaa | 54480 |
| catgatgaaa | ccccgtctct | actaaaaaaa | tagaaaaatt | agccaggcgt | ggtggcgggt | 54540 |
| acctgtaatc | caagctgctc | aggaggctga | ggcagaagaa | tcacttaaac | ccaagaggta | 54600 |
| gaagttgcag | tgagccgaga | ttgcaccact | gcactctagc | ctaggcgaca | gcgagactgc | 54660 |
| gtctcaaaaa | aaaaaaaaaa | gaacgttcca | aggtcaggac | taggcctccc | ctcagaagca | 54720 |
| gcaagtgaca | tatgtgacat | cctctccact | ccctatttgc | atttctaggt | tatataactg | 54780 |
| tactactatc | catgcatgcc | tactcttgtt | cccagggtga | aggacccaga | catggagagc | 54840 |
| cgaatccctg | caggccatta | taaatgagat | tatgccattt | gctcccattt | cttcttattc | 54900 |
| tttcattttt | ggggctctcc | atcttgatgt | gttctttgga | tcgtgaacag | atccaaagaa | 54960 |
| aaggttgttc | tgccgtgctg | tttgtcagga | tgaaaaactc | ttttttaagt | gtttaggtct | 55020 |
| gccccagtg | cccagcccaa | tcaagtaacg | tggtcaccca | gagtggcaga | taggagcaca | 55080 |
| aggcctggga | aagcactgga | gaaatgggat | ttgtttaaac | tatgacagca | ttatttcttg | 55140 |
| ttcccttgtc | cttttcctg | caagcaggaa | gggaacctga | ttggattacc | ccttctgatt | 55200 |
| gacaactatg | tgccccttt | ggagggactg | cctatcttca | ttcttcgact | agccactgag | 55260 |
| gtcagtgatc | aagcagatac | taagcatttc | ggtacatgca | tgtgtgctgg | agggaaaggg | 55320 |
| caaatgacca | ccctttgatc | tggaatgata | aagatgataa | gggtgggata | gctgaaggcc | 55380 |
| tgctctcatc | cccactaata | ttcattccca | gcaatattca | gcagtcccat | ttacagtttt | 55440 |
| aacgcctaaa | gtatcacatt | tcgttttta | gctttaagta | gtctgtgatc | tccgtttaga | 55500 |
| atgagaatgt | ttaaattcgt | acctattttg | aggtattgaa | tttctttgga | ccaggtgaat | 55560 |
| tgggacgaag | aaaaggaatg | ttttgaaagc | ctcagtaaag | aatgcgctat | gttctattcc | 55620 |
| atccggaagc | agtacatatc | tgaggagtcg | acctctcag | gccagcaggt | acagtggtga | 55680 |
| tgcacactgg | caccccagga | ctaggacagg | acctcataca | atctttagga | gatgaaactt | 55740 |

```
gcccatctct aaaatttcgg gatttctttg tacccaacaa ggttcaaaca caacagtcag     55800
cttttattca tgattttac  ttccatctgc tgatgtagaa catacctcca gagtgacctc     55860
agaaattgtc aaatgtgaaa acacaagcca tcacagtgag aaatgggagg ttgagttaga     55920
ttgtctaagg ctggagagtc catatactcc cactgttagc tctgaagtgt gtagccagtc     55980
ttcagattct gggtcagttg cctcagtctc tcttagcttt tgccttactc tttatccgac     56040
cactgccctg ccaggaaaac aaggctctat aactcctctt acaggtcagc ttgacacaaa     56100
aagggtgcct ggattcctaa tgtttcattg tcacttttcc cagtcagatg ataatgcttt     56160
tcaaatcaac atatattttg ggggaggttg aagggagag  ttgaaatatt ctaagaatca     56220
aagagtagcc cactttaatc agagtatgac ccctgattgc tcacagtcat ctcctgagca     56280
gtgtgagcga gttcagatg  aggaggctga aggccagtca ggcatgctcg aggattccaa     56340
gtctgtaggt gggagggcag agatttagtc ctgttggcca aagcctctag ggaatttctc     56400
actccagtgg agaaggcaac acacttacca aactgtgtgg aaactatctc atttgattag     56460
aaattttacc tcaagaagag gaaggacagt tgagaaagaa catttttctta cacatgagac    56520
agctaaggct tacaagaagg agaggaataa tgaggcaaaa taatcctcat taatattttc     56580
attcctcccc tggggattag aactactttc agacccgatt ttaatggtaa gttaggtact     56640
tcctacagtt gccatccaaa tatcagtcag gatcagacat gatgttagct cctgctacaa     56700
taaaaccatt ttctccctga atgaaaacaa aggttccaca ggagacagtc ccacagagca     56760
gtggcttctt ttcctcccctt taaaacctca tgttggctgg acacagtggc tcacacctgt     56820
aatcccagca ttttaggagg ctgaggtggg aagatggctt aagcccagga gtttgaggct     56880
gtagagctat gatcacacca ctgcccttca gcctgggtga cagagcaaga ccttgtctct     56940
aaataaacaa acaaacaaaa aatcctcttg tgttcaggcc tgtgggatcc cctgagaggc     57000
tagcccacaa gatccacttc aaaagcccta gataacacca agtctttcca gacccagtgc     57060
acatcccatc agccaggaca ccagtgtatg ttgggatgca aacagggagg cttatgacat     57120
ctaatgtgtt ttccagagtg aagtgcctgg ctccattcca aactcctgga agtggactgt     57180
ggaacacatt gtctataaag ccttgcgctc acacattctg cctcctaaac atttcacaga     57240
agatggaaat atcctgcagc ttgctaacct gcctgatcta tacaaagtct ttgagaggtg     57300
ttaaatatgg ttatttatgc actgtgggat gtgttcttct ttctctgtat tccgatacaa     57360
agtgttgtat caaagtgtga tatacaaagt gtaccaacat aagtgttggt agcacttaag    57420
acttatactt gccttctgat agtattcctt tatacacagt ggattgatta taaataaata    57480
gatgtgtctt aacataa                                                    57497

<210> SEQ ID NO 3
<211> LENGTH: 2662
<212> TYPE: RNA
<213> ORGANISM: Homo sapiens

<400> SEQUENCE: 3
gaagagaccc agcaacccac agaguugaga aauuugacug gcauucaagc uguccaauca      60
auagcugccg cugaagggug gggcuggaug gcguaagcua cagcugaagg aagaacguga     120
gcacgaggca cugaggugau uggcugaagg cacuuccguu gagcaucuag acguuuccuu     180
ggcucuucug gcgccaaaau gucguucgug gcaggggvua uucggcggcu ggacgagaca     240
guggugaacc gcaucgcggc gggggaaguu auccagcggc cagcuaaugc uaucaaagag     300
```

| | |
|---|---:|
| augauugaga acuguuuaga ugcaaaaucc acaaguauuc aagugauugu uaaagaggga | 360 |
| ggccugaagu ugauucagau ccaagacaau ggcaccggga ucaggaaaga agaucuggau | 420 |
| auuguaugug aaagguucac acuaguaaaa cugcagaccu uugaggauuu agccaguauu | 480 |
| ucuaccuaug gcuuucgagg ugaggcuuug gccagcauaa gccauguggc ucauguuacu | 540 |
| auuacaacga aaacagcuga uggaaagugu gcauacagag caaguuacuc agauggaaaa | 600 |
| cugaaagccc cuccuaaacc augugcuggc aaucaaggga cccagaucac gguggaggac | 660 |
| cuuuuuuaca acauagccac gaggagaaaa gcuuuaaaaa uccaaguga agaauauggg | 720 |
| aaaauuuugg aaguuguugg cagguauuca guacacaaug caggcauuag uuucucaguu | 780 |
| aaaaaacaag gagagacagu agcugauguu aggacacuac ccaaugccuc aaccguggac | 840 |
| aauauucgcu ccaucuuugg aaaugcuguu agucgagaac ugauagaaau uggaugugag | 900 |
| gauaaaaccc uagccuucaa aaugaauggu uacauauccca augcaaacua cucagugaag | 960 |
| aagugcaucu ucuuacucuu caucaaccau cgucugguag aaucaacuuc cuugagaaaa | 1020 |
| gccauagaaa caguguaugc agccauuuug cccaaaaaca cacacccauu ccuguaccuc | 1080 |
| aguuuagaaa ucagucccca gaauguggau guuaaugugc accccacaaa gcaugaaguu | 1140 |
| cacuuccugc acgaggagag cauccuggag cgggugcagc agcacaucga gagcaagcuc | 1200 |
| cugggcucca auccuccag gauguacuuc acccagacuu ugcuaccagg acuugcuggc | 1260 |
| cccucuggggg agauggguuaa auccacaaca agucugaccu cgucuucuac uucuggaagu | 1320 |
| agugauaagg ucuaugccca ccagauggau cguacagauu cccgggaaca gaagcuugau | 1380 |
| gcauuucugc agcccucgag caaaccccug ccagucagc cccaggccau ugucacagag | 1440 |
| gauaagacag auauuucuag uggcagggcu aggcagcaag augaggagau gcuugaacuc | 1500 |
| ccagccccug cugaaguggc ugccaaaaau cagagcuugg aggggauac aacaaagggg | 1560 |
| acuucagaaa ugucagagaa gagaggaccu acuuccagca accccagaaa gagacaucgg | 1620 |
| gaagauucug augggaaau ggugaagau gauucccgaa aggaaaugac ugcagcuugu | 1680 |
| accccccgga gaaggaucau uaaccucacu agauguuuga gucuccagga agaaauuaau | 1740 |
| gagcagggac augagguucu ccgggagaug uugcauaacc acuccuucgu gggcuguguag | 1800 |
| aauccucagu gggccuuggc acagcaucaa accaaguuau accucucaa caccaccaag | 1860 |
| cuuagugaag aacuguucua ccagauacuc auuuaugauu uugccaauuu uggguuucuc | 1920 |
| agguuaucgg agccagcacc gcucuuugac cuugccaugc uugccuuaga uaguccagag | 1980 |
| aguggcugga cagaggaaga uggucccaaa gaaggacuug cugaauacau guuagguuu | 2040 |
| cugaagaaga aggcugagau gcuugcagac uauuucucuu uggaaauuga ugaggaaggg | 2100 |
| aaccugauug gauucccccu ucugauugac aacuaugugc cccuuuggga gggacugccu | 2160 |
| aucuucauuc uucgacuagc cacgagugug aauugggacg aagaaaagga auguuuugaa | 2220 |
| agccucagua agaaugcgc uauguucuau ccauccgga agcaguacau aucugaggag | 2280 |
| ucgacccucu caggccagca gagugaagug ccuggccucca uuccaaacuc cuggaagugg | 2340 |
| acugugggaac acauugucua uaaagccuug cgcucacaca uucugccucc uaaacauuuc | 2400 |
| acagaagaug gaaauauccu gcagcuugcu aaccugccug aucuauacaa agucuuugag | 2460 |
| aggguuaaaa uauggguuauu uaugcacugu gggauguguu cuucuuucuc uguauuccga | 2520 |
| uacaaagugu uguaucaaag ugugauauac aaaguguacc aacauaagug uugguagcac | 2580 |
| uuaagacuua uacuugccuu cugauagaau uccuuuauac acagugauu gauuauaaau | 2640 |
| aaauagaugu gucuuaacau aa | 2662 |

<210> SEQ ID NO 4
<211> LENGTH: 2271
<212> TYPE: DNA
<213> ORGANISM: Homo sapiens

<400> SEQUENCE: 4

| | | | | | |
|---|---|---|---|---|---|
| atgtcgttcg | tggcaggggt | tattcggcgg | ctggacgaga | cagtggtgaa | ccgcatcgcg | 60 |
| gcggggaag | ttatccagcg | ccagctaat | gctatcaaag | atgatgattga | gaactgttta | 120 |
| gatgcaaaat | ccacaagtat | tcaagtgatt | gttaagagg | gaggcctgaa | gttgattcag | 180 |
| atccaagaca | atggcaccgg | gatcaggaaa | gaagatctgg | atattgtatg | tgaaaggttc | 240 |
| actactagta | aactgcagtc | ctttgaggat | ttagccagta | tttctaccta | tggctttcga | 300 |
| ggtgaggctt | tggccagcat | aagccatgtg | gctcatgtta | ctattacaac | gaaaacagct | 360 |
| gatggaaagt | gtgcatacag | agcaagttac | tcagatggaa | aactgaaagc | ccctcctaaa | 420 |
| ccatgtgctg | gcaatcaagg | gacccagatc | acggtggagg | accttttta | caacatagcc | 480 |
| acgaggagaa | aagctttaaa | aaatccaagt | gaagaatatg | ggaaaatttt | ggaagttgtt | 540 |
| ggcaggtatt | cagtacacaa | tgcaggcatt | agtttctcag | ttaaaaaaca | aggagagaca | 600 |
| gtagctgatg | ttaggacact | acccaatgcc | tcaaccgtgg | acaatattcg | ctccatcttt | 660 |
| ggaaatgctg | ttagtcgaga | actgatgaaa | attggatgtg | aggataaaac | cctagccttc | 720 |
| aaaatgaatg | gttacatatc | caatgcaaac | tactcagtga | agaagtgcat | cttcttactc | 780 |
| ttcatcaacc | atcgtctggt | agaatcaact | tccttgagaa | aagccataga | aacagtgtat | 840 |
| gcagcctatt | tgcccaaaaa | cacacaccca | ttcctgtacc | tcagtttaga | aatcagtccc | 900 |
| cagaatgtgg | atgttaatgt | gcaccccaca | aagcatgaag | ttcacttcct | gcacgaggag | 960 |
| agcatcctgg | agcgggtgca | gcagcacatc | gagagcaagc | tcctgggctc | caattcctcc | 1020 |
| aggatgtact | tcacccagac | tttgctacca | ggacttgctg | gccctctgg | ggagatggtt | 1080 |
| aaatccacaa | caagtctgac | ctcgtcttct | acttctggaa | gtagtgataa | ggtctatgcc | 1140 |
| caccagatgg | atcgtacaga | ttcccgggaa | cagaagcttg | atgcatttct | gcagcctctg | 1200 |
| agcaaacccc | tgtccagtca | gccccaggcc | attgtcacag | aggataagac | agatatttct | 1260 |
| agtggcaggg | ctaggcagca | agatgaggag | atgcttgaac | tcccagcccc | tgctgaagtg | 1320 |
| gctgccaaaa | atcagagctt | ggaggggat | acaacaaagg | ggacttcaga | aatgtcagag | 1380 |
| aagagaggac | ctacttccag | caaccccaga | aagagacatc | gggaagattc | tgatgtggaa | 1440 |
| atggtggaag | atgattcccg | aaaggaaatg | actgcagctt | gtacccccg | gagaaggatc | 1500 |
| attaacctca | ctagtgtttt | gagtctccag | gaagaaatta | atgagcaggg | acatgaggtt | 1560 |
| ctccgggaga | tgttgcataa | ccactccttc | gtgggctgtg | tgaatcctca | gtgggccttg | 1620 |
| gcacagcatc | aaaccaagtt | ataccttctc | aacaccacca | agcttagtga | agaactgttc | 1680 |
| taccagatac | tcatttatga | ttttgccaat | tttggtgttc | tcaggttatc | ggagccagca | 1740 |
| ccgctctttg | accttgccat | gcttgcctta | gatagtccag | agagtggctg | gacagaggaa | 1800 |
| gatggtccca | agaaggact | tgctgaatac | attgttgagt | ttctgaagaa | gaaggctgag | 1860 |
| atgcttgcag | actatttctc | tttggaaatt | gatgaggaag | ggaacctgat | tggattaccc | 1920 |
| cttctgattg | acaactatgt | gcccccttg | gagggactgc | ctatcttcat | tcttcgacta | 1980 |
| gccactgagg | tgaattggga | cgaagaaaag | gaatgttttg | aaagcctcag | taaagaatgc | 2040 |
| gctatgttct | attccatccg | gaagcagtac | atatctgagg | agtcgaccct | ctcaggccag | 2100 |

```
cagagtgaag tgcctggctc cattccaaac tcctggaagt ggactgtgga acacattgtc    2160
tataaagcct tgcgctcaca cattctgcct cctaaacatt tcacagaaga tggaaatatc    2220
ctgcagcttg ctaacctgcc tgatctatac aaagtctttg agaggtgtta a             2271

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
cagactttgc taccaggact tgc                                              23

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ctgcctagcc ctgccactag                                                  20

<210> SEQ ID NO 7
<211> LENGTH: 24
<212> TYPE: DNA
<213> ORGANISM: Homo sapiens

<400> SEQUENCE: 7
accagatgga tcgtacagat tccc                                             24

<210> SEQ ID NO 8
<211> LENGTH: 24
<212> TYPE: DNA
<213> ORGANISM: Homo sapiens

<400> SEQUENCE: 8
accagatgga tcgtacagat tccc                                             24
```

METHOD FOR EVALUATING THE EFFICACY OF AN EGFR-TKI TREATMENT

BACKGROUND

Technical Field

The present invention relates to a method for evaluating the efficacy of a cancer therapy. More specifically, the present invention relates to a method for evaluating the efficacy of an EGFR-TKI treatment and estimating the progression-free survival of a subject.

REFERENCE TO SEQUENCE LISTING SUBMITTED VIA EFS-WEB

This application includes an electronically submitted sequence listing in .txt format. The .txt file contains a sequence listing entitled "20170201_50250234PUS2_ST25.txt" created on Feb. 1, 2017 and is 88,974 bytes in size. The sequence listing contained in this .txt file is part of the specification and is hereby incorporated by reference herein in its entirety.

Description of Related Art

Lung cancer has high incidence rates worldwide, and its 5-year survival is dismal as most cases are diagnosed at late stages. Chemotherapy, although with limited efficacy, used to be the main treatment option for patients with advanced lung cancer. In 2004, somatic mutations were reported to exist in the tyrosine kinase domain of epidermal growth factor receptor (EGFR) in tumors of a subset of patients with non-small cell lung cancer (NSCLC) who responded dramatically to EGFR tyrosine kinase inhibitors (TKIs). This discovery has opened a new era of targeted therapy for NSCLC. Nowadays, EGFR-TKIs are used as the standard first-line therapy for patients with advanced lung adenocarcinoma harboring activating EGFR mutations, and they remarkably improve the survival and quality of life in patients with these driver mutations.

Drug resistance is a major obstacle in targeted cancer therapy, and understanding the mechanisms of resistance is pivotal for developing more effective treatment strategies. Around 70% of patients with lung adenocarcinoma that has activating EGFR mutations (mostly a small in-frame deletion in exon 19 and a substitution mutation L858R) display objective clinical response to EGFR-TKI treatment. However, despite the initial disease control, tumor relapse is inevitably observed after a median of 9-14 months, indicating the development of acquired resistance to EGFR-TKIs in these patients. Studies have identified different mechanisms of acquired EGFR-TKI resistance, including a second-site EGFR T790M mutation, MET amplification, PIK3CA mutations, epithelial-to-mesenchymal transitions and conversion to small cell carcinoma. On the other hand, ~30% patients with TM-sensitive EGFR mutations fail to demonstrate objective tumor regression on initial EGFR-TKI therapy and are defined as having primary or intrinsic resistance. Some co-existing genetic variations have been implicated in the mechanism of TM insensitivity in EGFR-mutant patients, including de novo presence of EGFR T790M or MET amplification, KRAS mutations, loss of PTEN, and a germline deletion polymorphism of BIM. However, the majority of resistant cases cannot be explained by these variations and the mechanistic basis for intrinsic EGFR-TM resistance in patients supposed to be responsive is still largely unknown.

In light of the high death rate of cancer and the expensive cost for cancer therapy (especially, targeted therapy), there is continuously a need for a method for evaluating the efficacy of an EGFR-TM treatment before or after the treatment.

SUMMARY

In light of the foregoing, one of the objects of the present invention is to provide a method for evaluating the efficacy of an EGFR-TM treatment so that the patients in need can be screened before the treatment to prevent from investing costs in ineffective therapy.

Another object of the present invention is to provide a method for evaluating a progression-free survival of a subject so that the follow-up treating strategies can be set up as soon as possible after an EGFR-TKI treatment.

In order to achieve the above-mentioned objects, the present invention provides a method for evaluating the efficacy of an EGFR-TKI treatment to a subject, comprising: (A) providing a sample from said subject; (B) analyzing a sequence of MLH1 DNA, a sequence of MLH1 mRNA, and/or a cDNA sequence from said MLH1 mRNA of said sample, to identify an alteration at V384 of an encoded MLH1 protein; or analyzing a MLH1 protein of said sample to identify an alteration at V384 of said MLH1 protein; provided that when said alteration is identified, a response rate of said subject to said EGFR-TKI treatment is from 0% to 50%; or provided that when said alteration is identified, said progression-free survival of said subject is 1.5 to 8.7 months; whereas, when said alteration is not identified, said progression-free survival of said subject is 8.8 to 12.5 months.

Preferably, said alteration at V384 is V384D.

Preferably, said alteration corresponds with a T1349 mutation of said MLH1 mRNA. Preferably, said T1349 mutation is a T1349A mutation.

Preferably, said alteration corresponds with a T1151 mutation of said cDNA. Preferably, said T1151 mutation is a T1151A mutation.

Preferably, said analyzing is performed by polymerase chain reaction, Southern blot, Western blot, or a combination thereof.

Preferably, said analyzing is performed by using an antibody, a primer set, a probe, or a combination thereof.

Preferably, said method is conducted before and/or after said EGFR-TKI treatment.

The present invention also provides a method for estimating a progression-free survival of a subject, comprising: (A) providing a sample from said subject; (B) analyzing a sequence of MLH1 DNA, a sequence of MLH1 mRNA, and/or a cDNA sequence from said MLH1 mRNA of said sample, to identify an alteration at V384 of an encoded MLH1 protein; or analyzing a MLH1 protein of said sample to identify an alteration at V384 of said MLH1 protein; provided that when said alteration is identified, said progression-free survival of said subject is 1.5 to 8.7 months; or when said alteration is not identified, said progression-free survival of said subject is 8.8 to 12.5 months.

Preferably, said alteration at V384 is V384D.

Preferably, said alteration corresponds with a T1151 mutation of said MLH1 mRNA. Preferably, said T1151 mutation is a T1151A mutation.

Preferably, said alteration corresponds with a T1151 mutation of said cDNA. Preferably, said T1151 mutation is a T1151A mutation.

Preferably, said analyzing is performed by polymerase chain reaction, Southern blot, Western blot, or a combination thereof.

Preferably, said analyzing is performed by using an antibody, a primer set, a probe, or a combination thereof. Preferably, said primer set comprises SEQ ID NO: 05 and SEQ ID NO: 06.

Preferably, said subject has been treated with an EGFR-TKI treatment.

Preferably, said subject suffers from lung cancer or is suspected to suffer from lung cancer.

To sum up, the present invention identifies the correlation between the MLH1 V384D mutation with the poor efficacy and short progression-free survival of an EGFR-TKI treatment. By applying this information in evaluating the efficacy of an EGFR-TKI treatment before or after treatment and in estimating a progression-free survival of a subject can provide better treating strategies for patients in need.

DETAILED DESCRIPTION

Figure 1A:
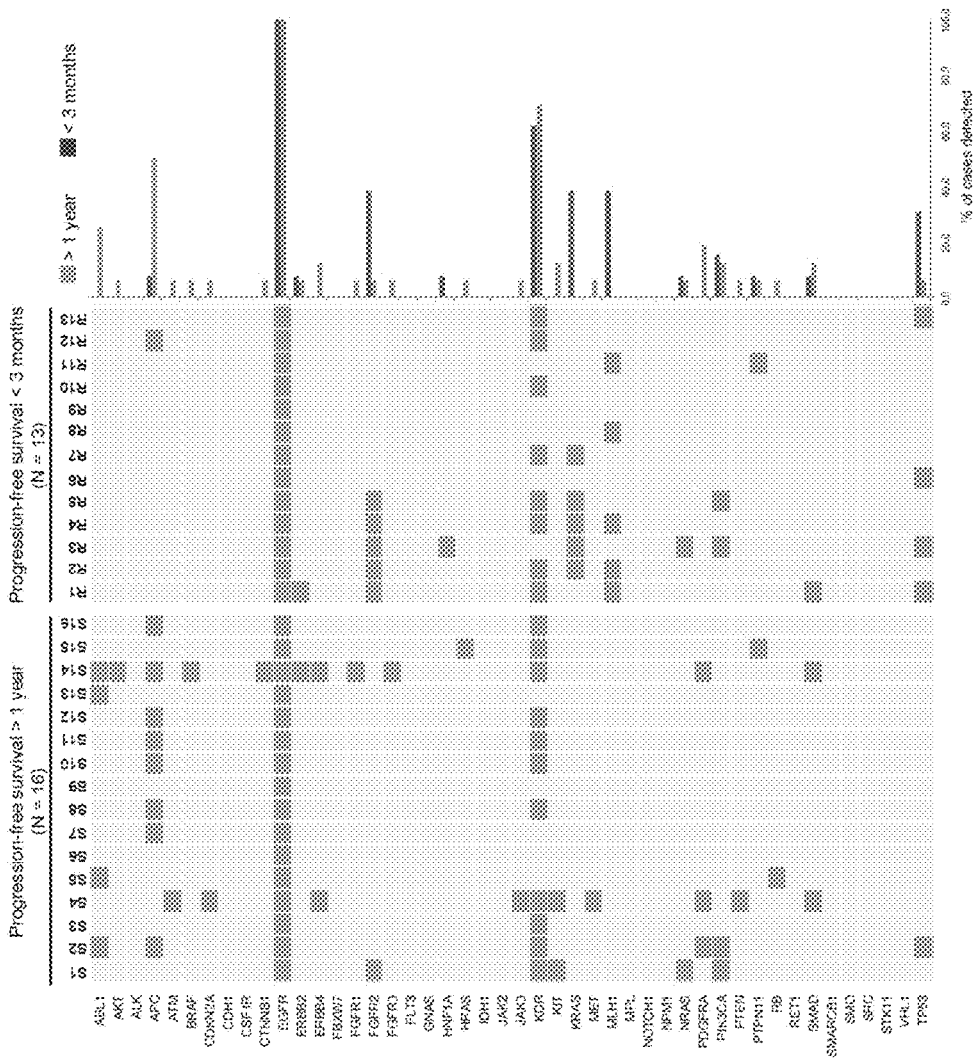
FIG. 1A shows the results of Next-Generation Sequencing in Example 2 for comparing patients having PFS>1 year (N=16) with patients having PFS<3 months (N=13).

In this study, we hypothesized that specific genetic alterations may underlie the primary resistance to EGFR-TKIs in lung adenocarcinoma harboring activating EGFR mutations. Towards uncovering such genetic determinants of treatment resistance, we performed Next-Generation Sequencing (NGS)-based mutation profiling of lung adenocarcinoma with the EGFR L858R mutation from patients who received EGFR-TKI therapy, and searched for genetic variants/mutations that could differentiate patients displaying primary resistance to EGFR-TKIs from those having a durable response.

The term of "EGFR-TKI therapy" or "EGFR-TKI treatment" used herein is referred to as a targeted therapy or targeted treatment adopting the fact that a fair amount of non-small cell lung cancer patients share a somatic mutation in the tyrosine kinase domain of epidermal growth factor receptor of tumor cells. Specifically, the "EGFR-TKI therapy" or "EGFR-TKI treatment" is conducted by using an EGFR tyrosine kinase inhibitor targeting the somatic mutation in the tyrosine kinase domain of epidermal growth factor receptor of tumor cells.

The term of "efficacy of an EGFR-TKI treatment" used herein is referred to as the effect of an EGFR-TKI treatment on the progression of tumors. The "efficacy of an EGFR-TKI treatment" can be determined by the response rate of the patient concerned to said EGFR-TKI treatment. After being treated by EGFR-TKI treatment, if the tumor size of the patient decreased at least 20% from the initial size there of before treatment in 3 months, the patient is deemed as response to the treatment. The response rate can be calculated by the number of patients having response out of the total number of the patient monitored.

The other way to determine the efficacy of an EGFR-TKI treatment is by observing the "progression-free survival" of the patient concerned. The term of "progression-free survival" used herein is referred to as the time period between the initial date of a treatment and the time point that the tumor concerned begins to progress again. In other words, it is the length of time that the tumors, during this time period, have no progression or are reduced in size.

The term of "analyzing" or "analyze" used herein is referred to as evaluating or examining a property of a subject of interest by at least of technical means. Said technical means include but not limited to polymerase chain reaction, Southern blot, and Western blot.

The term of "V384" used herein is referred to as the 384$^{th}$ amino acid of the amino acid sequences of MLH1 protein; wherein "V" is the one-letter abbreviation of Valine (Val). The term of "alteration at V384" used herein is referred to as the 384$^{th}$ amino acid of Valine is altered to another amino acid other than Valine. The term of "alteration at V384D" used herein is referred to as the 384$^{th}$ amino acid of Valine is altered to Aspartic acid; wherein "D" is the one-letter abbreviation of Aspartic acid (Asp). See also SEQ ID NO: 01 for the amino acid sequence having the aforesaid mutation and SEQ ID NO: 02 for the DNA sequence having the aforesaid mutation.

The term of "T1349" used herein is referred to as the 1349$^{th}$ nucleotide of the nucleotide sequence of a mRNA encoding a MLH1 protein; "T" is an abbreviation of thymine. The term of "T1349 mutation" used herein is referred to as the 1349$^{th}$ nucleotide of thymine is altered/mutated to another nucleotide other than thymine. The term of "alteration at T1349A" used herein is referred to as the 1349$^{th}$ nucleotide of thymine is altered to adenine; wherein "A" is an abbreviation of adenine. See also SEQ ID NO: 03 for the mRNA sequence having the aforesaid mutation.

The term of "T1151" used herein is referred to as the 1151$^{th}$ nucleotide of the nucleotide sequence of a cDNA; wherein said cDNA is from a mRNA encoding a MLH1 protein; "T" is an abbreviation of thymine. The term of "T1151 mutation" used herein is referred to as the 1151$^{th}$ nucleotide of thymine is altered/mutated to another nucleotide other than thymine. The term of "alteration at T1151A" used herein is referred to as the 1151$^{th}$ nucleotide of thymine is altered to adenine; wherein "A" is an abbreviation of adenine. See also SEQ ID NO: 04 for the cDNA sequence having the aforesaid mutation.

The present invention identifies the correlation between the mutation at V384 of MHL1 with the poor efficacy of EGFR-TKI treatment of a patient.

In one aspect of the present invention, a method for evaluating the efficacy of an EGFR-TKI treatment to a subject is provided. In another aspect of the present invention, a method for estimating a progression-free survival of a subject is provided.

The method for evaluating the efficacy of an EGFR-TKI treatment to a subject comprises (A) providing a sample from said subject; and (B) analyzing a sequence of MLH1 DNA, a sequence of MLH1 mRNA, and/or a cDNA sequence from said MLH1 mRNA of said sample, to identify an alteration at V384 of an encoded MLH1 protein; or analyzing a MLH1 protein of said sample to identify an alteration at V384 of said MLH1 protein; provided that when said alteration is identified, a probability that said EGFR-TKI treatment has efficacy to said subject is from 0% to 50%; or provided that when said alteration is identified, said progression-free survival of said subject is 1.5 to 8.7 months; or when said alteration is not identified, said progression-free survival of said subject is 8.8 to 12.5 months.

Said sample is collected from a subject concerned and it could be from tumor tissues or blood of said subject. Said subject may be a patient suffering from cancer (preferably, non-small cell lung cancer). In an alternative embodiment of the present invention, the aforesaid methods can be conducted before or after an EGFR-TKI treatment. Preferably, the aforesaid methods are conducted before an EGFR-TKI treatment so that the aforesaid methods are served as a pre-evaluation for testing if the subject is suitable for the EGFR-TKI treatment. In this way, the cost for the EGFR-TKI treatment can be saved (if the subject concerned is found not suitable for the EGFR treatment) and proper treating strategies can be set up as earlier as possible.

In an alternative embodiment, the mutation at V384 may be an alteration of Valine to any other amino acid. Correspondingly, the nucleotide sequence of the mRNA encoding the MLH1 protein at the V384 position may be altered from GUU, GUC, GUA, or GUG to any codon other than GUU, GUC, GUA, or GUG. Also, the nucleotide sequence of the cDNA from said mRNA encoding the MLH1 protein at the V384 position may be correspondingly altered from GTT, GTC, GTA, or GTG to any codon other than GTT, GTC, GTA, or GTG.

In a preferable embodiment, the mutation at V384 of MHL1 is an alteration of Valine to Aspartic acid. Correspondingly, the nucleotide sequence of said mRNA is altered to GAU or GAC. Also, the nucleotide sequence of said cDNA is correspondingly altered to GAT or GAC.

The aforesaid alteration of V384 can be detected by Western blot via a suitable antibody. In an alteration embodiment, the alteration of V384 can be detected by analyzing the DNA, mRNA, or cDNA of MLH1 via polymerase chain reaction, Southern blot, or any well-understood technical manners in the art; wherein a suitable primer set or probe can be used in the analysis.

Example 1: Research Preparation

[Patients and Study Design]

Patients were included if they had primary lung adenocarcinoma harboring the L858R mutation without a co-existing T790M mutation in EGFR and received their first-time EGFR-TKI treatment at Taipei Veterans General Hospital during the period from January 2009 to January 2013. Patients who had prior EGFR-TKI therapy or received EGFR-TKI in combination with other anti-cancer treatment were excluded. Patients who had adequate tumor specimens for further molecular testing were enrolled. This study was approved by the Institution Review Board of Taipei Veterans General Hospital.

The size of the tumor is monitored for at least two months after the initiation of EGFR-TKI therapy and usually measured approximately three months after the initiation of treatment. If tumors progressed within the aforesaid period, we considered that the treatment was clinically ineffective and that these patients presented primary (or intrinsic) resistance. To discover candidate genetic variations that may associate with primary EGFR-TKI resistance in EGFR mutant tumors, we performed genomic profiling of EGFR L858R tumors from 16 patients with long (>1 year) progression-free survival (PFS) and 13 patients with short (<3 months) PFS. NGS was performed to screen through a cancer-related gene mutation panel (Ion AmpliSeq Cancer Panel, Ion Torrent, Life Technologies); 739 mutation hotspot regions within 46 key cancer-related genes from the COSMIC database were examined. Distributions of genomic variants in the two groups of patients were compared. Genes with differential mutation status between two groups were further investigated in a total of 158 EGFR L858R tumors by PCR amplification and direct Sanger sequencing, and the association of candidate variants with differential tumor response to EGFR-TKIs was explored.

[Histopathology Review and Sample Preparation]

Consecutive tissue sections were prepared from each archived formalin-fixed to paraffin-embedded (FFPE) pathology specimen and reviewed by pathologists; tumor areas were marked on deparaffinized unstained sections and manually dissected. Proteinase K-digested tissue extracts were subjected to genomic profiling tests. Genomic DNA was also prepared from available blood samples using the illustra blood genomicPrep Mini Spin Kit (GE Healthcare Life Sciences) according to the manufacturer's protocol.

[Statistical Analysis]

The objective tumor response was evaluated according to the revised RECIST criteria. PFS was calculated from the date of starting EGFR-TKI therapy to the date of disease progression or death. The association between patient characteristics and MLH1 mutation status was analyzed by chi-square and Fisher's exact tests. Kaplan-Meier survival curves were constructed and compared using the log-rank test. Cox regression models were built using a backward stepwise procedure for multivariate survival analysis. Analyses were carried out using PASW Statistics 18.0 (SPSS Inc., Chicago, Ill.).

Example 2: Forty-Six-Gene Mutation Profiles of EGFR L858R-Positive Lung Adenocarcinomas Next-generation sequencing (NGS) was used to interrogate mutations within hotspot regions of 46 cancer-related genes in lung adenocarcinoma samples from 13 and 16 EGFR-TKI-treated patients who had short (<3 months) and long (>1 year) PFS, respectively.

[Next-Generation Sequencing]

Genomic DNA from FFPE tumor tissues was quantified using the Qubit® dsDNA HS Assay Kit and the Qubit® fluorometer (Life Technologies); 10 nanograms were amplified by multiplex PCR using the Ion AmpliSeq Cancer Panel Primers Pool (Life Technologies). PCR amplicons were ligated with barcode adaptors using the Ion Xpress Barcode Adapters 1-16 Kit (Life Technologies), and subjected to emulsion PCR. Template was prepared by the automated Ion OneTouch System using the Ion OneTouch 200 Template Kit v2 DL, and DNA was sequenced on a 316 chip using the Ion PGM Sequencing Kit v2 and the Ion Torrent Personal Genome Machine (PGM, Ion Torrent, Life Technologies). Data were analyzed using the Torrent Suite software v3.0 and the Ion Torrent Variant Caller software v3.0. Variants were called when a minimum coverage of 500 reads was achieved and at least 5% of variant reads were identified.
[Results]

Figure 1B:
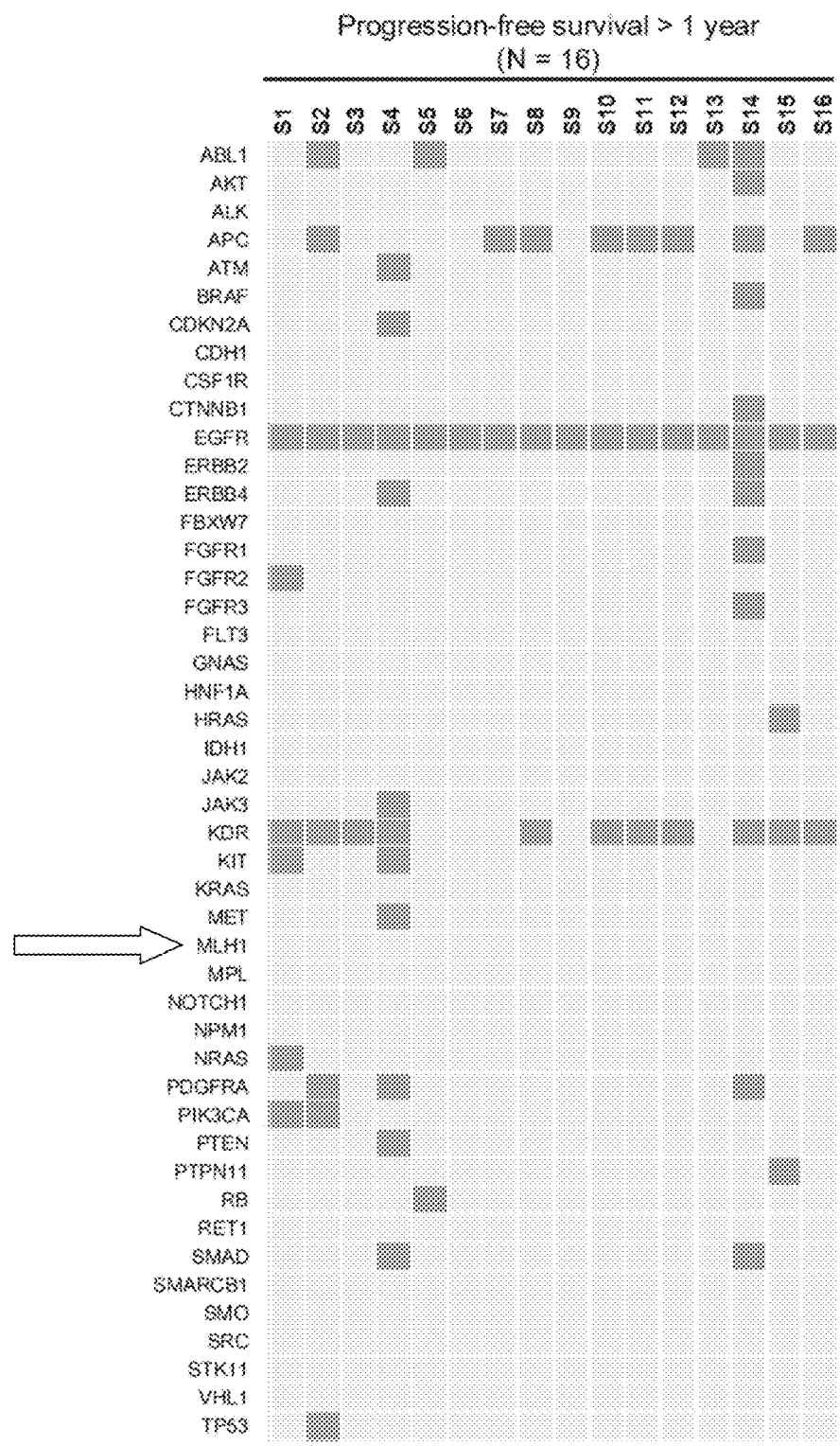
FIG. 1B shows the magnified image of the left chart of FIG. 1A (patients having PFS>1 year).
Figure 1C:
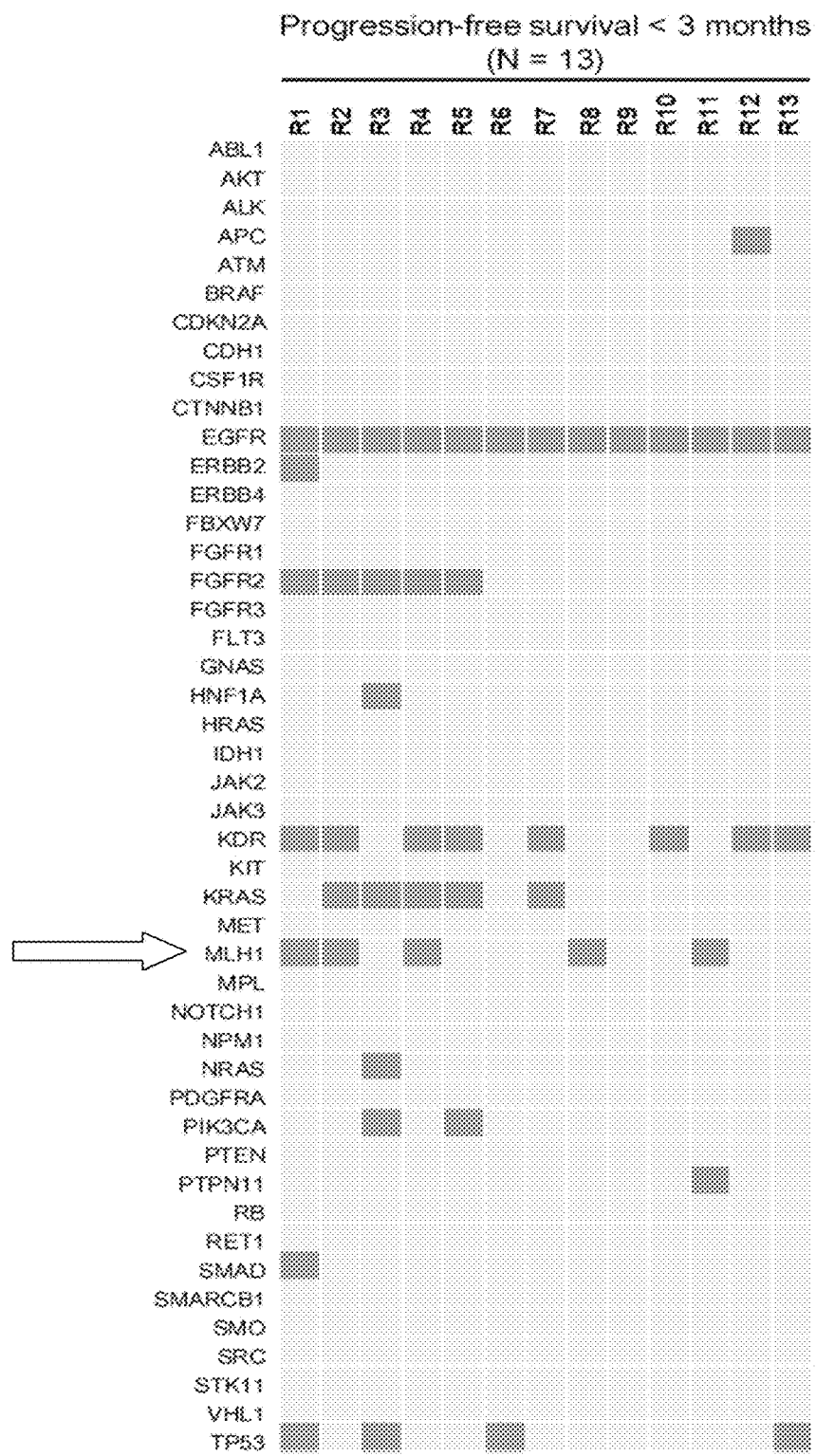
FIG. 1C shows the magnified image of the middle chart of FIG. 1A (patients having PFS<3 months).
Figure 1D:
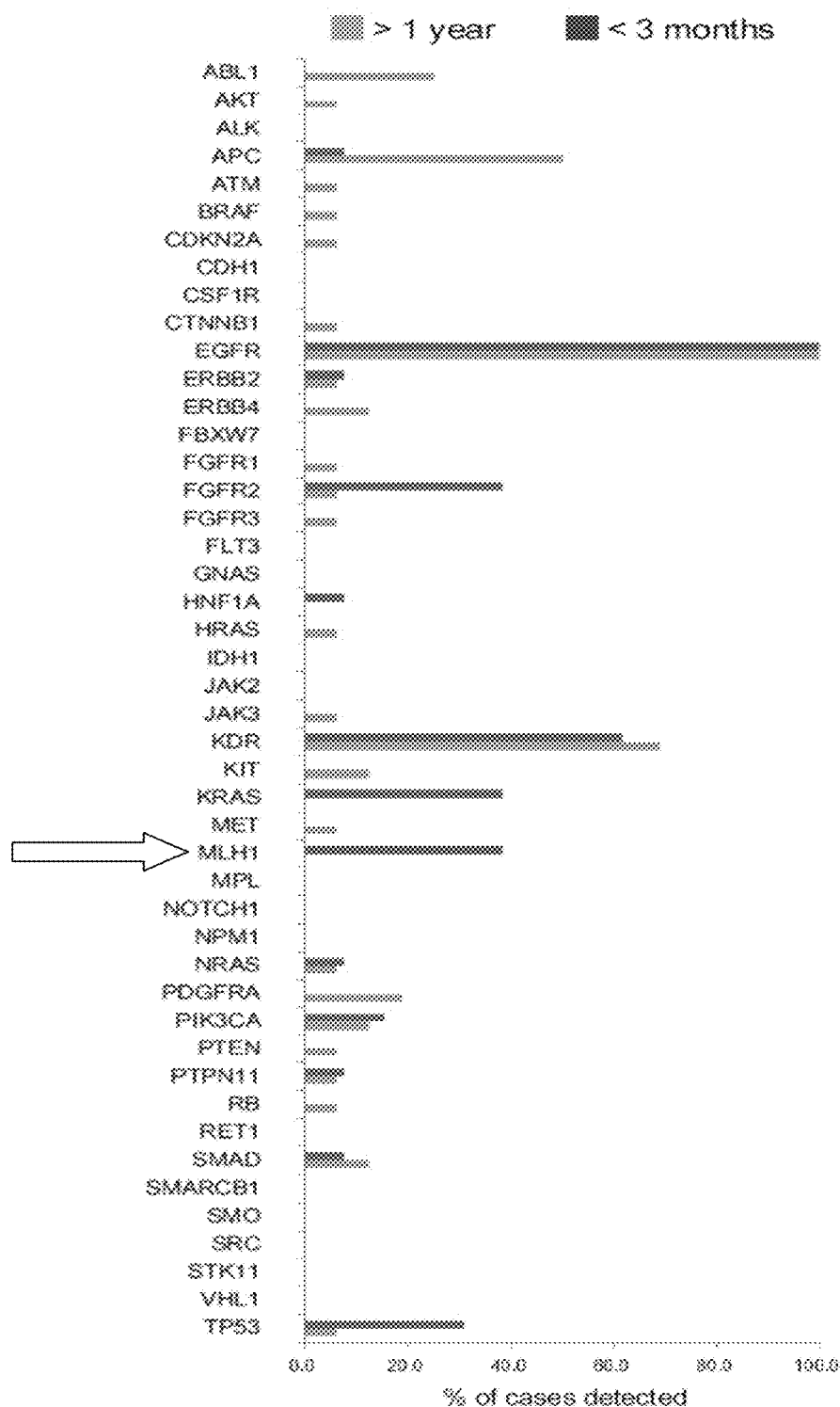
FIG. 1D shows the magnified image of the right chart of FIG. 1A (the bar chart).
Figure 1E:
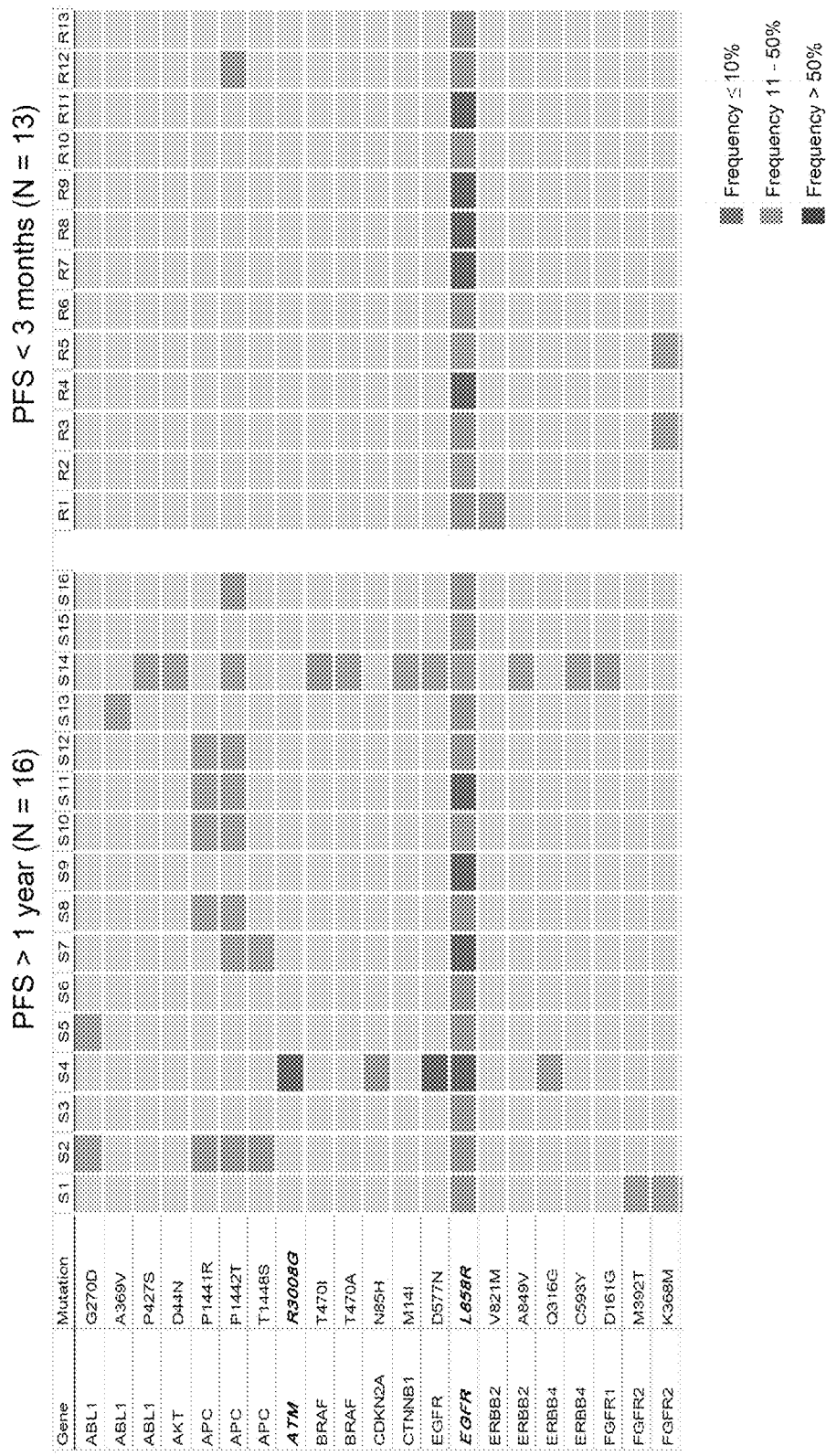
FIG. 1E shows more details of the results of the Next-Generation Sequencing in Example 2, including the mutation of the listing genes and the frequency thereof.
Figure 1E:
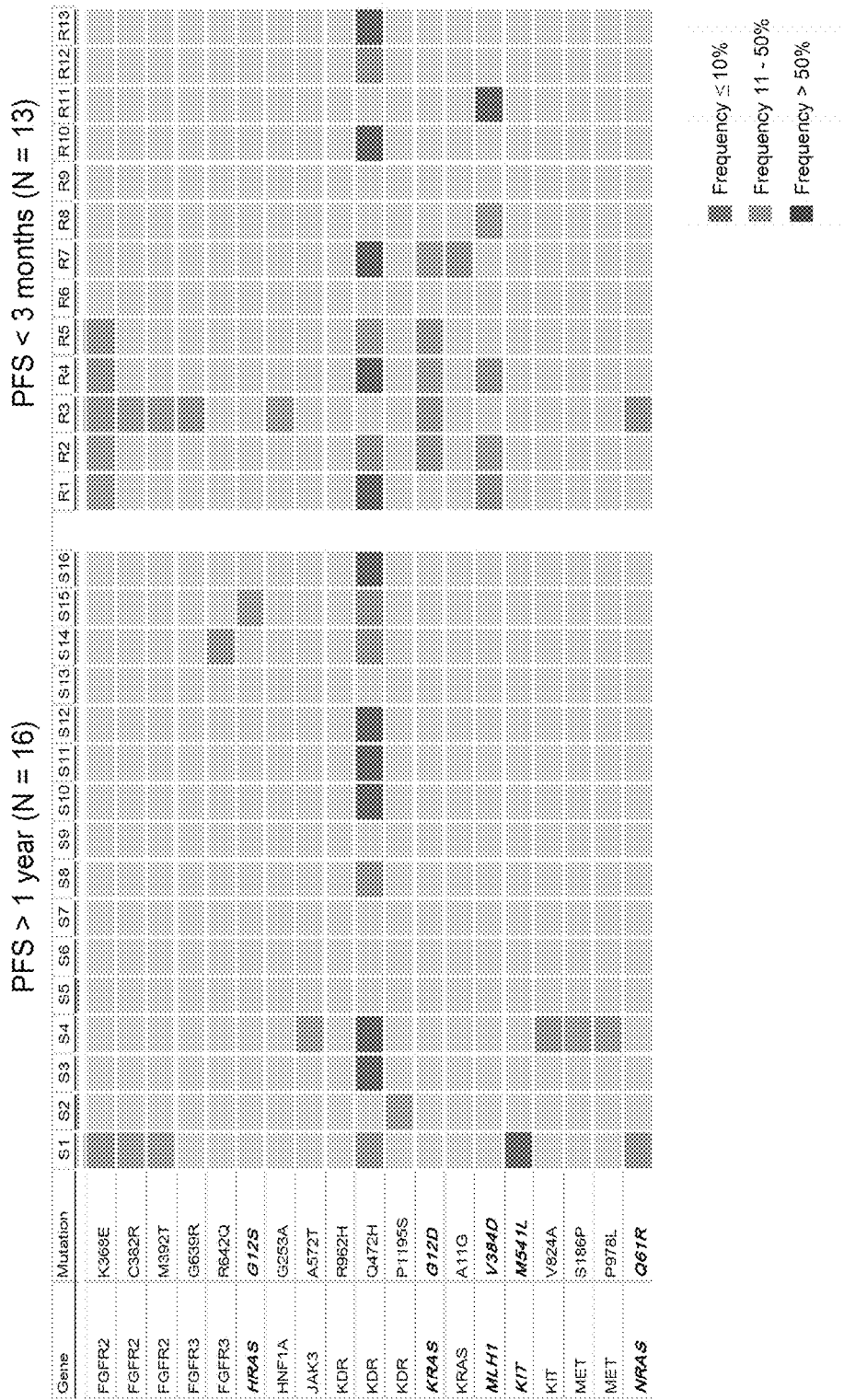
Figure 1E:
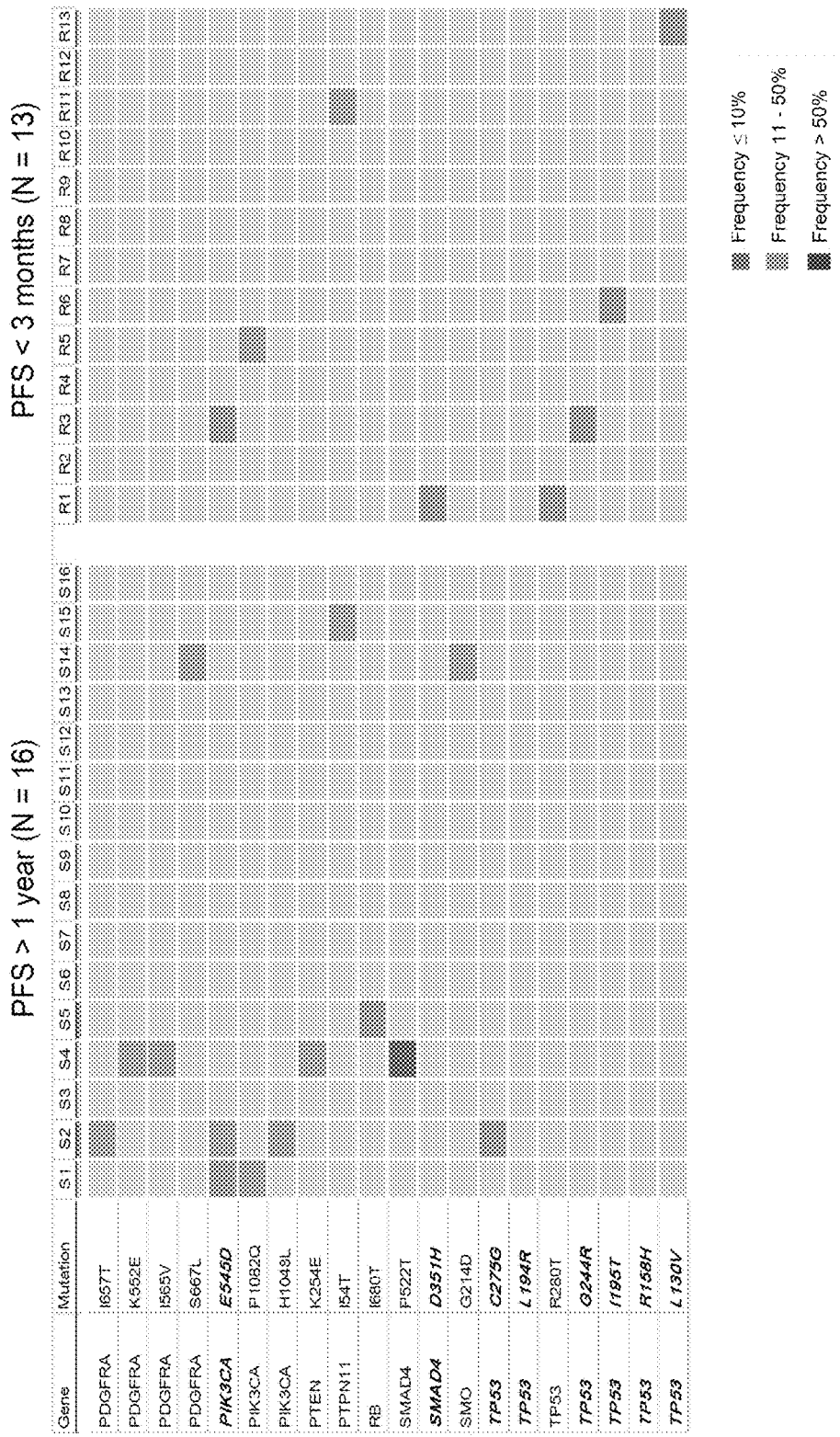

The results were show in FIG. 1A and more details in FIG. 1E. Moreover, the results showed in FIG. 1A were magnified and separately shown in FIGS. 1B, 1C and 1D.

Differential mutation patterns were revealed in these two groups (that is, long PFS and short PFS). All 29 tumors (16 patients with long (>1 year) PFS and 13 patients with short (<3 months) PFS) were confirmed to harbor the activating EGFR L858R mutation without the simultaneous presence of the T790M allele that predicts EGFR-TKI resistance. Among the 46 genes, KDR (which encodes for vascular endothelial growth factor receptor 2) was the most commonly mutated gene coexisting with EGFR L858R, regardless of the patient's treatment response. Mutation rates of ABL1, APC, and PDGFRA were disproportionately high in the patient with long PFS. In contrast, mutations in FGFR2 (K368E), KRAS (G12D), MLH1 (V384D), and TP53 occurred more often in patients with short PFS. Derepression of FGFR2 expression has been implicated in the mechanism for rapidly acquired EGFR-TKI resistance in NSCLC cells. KRAS G12C is linked to poor outcomes of EGFR-TKI therapy in NSCLC patients.

With regard to FIG. 1E, amino acids variations within the hotspot regions of 46 cancer-related genes in individual EGFR L858R tumors are shown on the left in 2 groups, according to the progression-free survival (PFS) of patients. Frequencies of individual genetic variations detected by the IonTorrent software were grouped into three ranges and shown in different colors. Variations shown in bold and italic are hotspot mutations published in the COSMIC database.

The results shown in FIGS. 1A, 1B, 1C, 1D and 1E indicates the association between the DNA mismatch repair gene MLH1 and EGFR-TKI resistance, which was never known before the present research.

Example 3: MLH1 V384D in Patients with Primary Lung Adenocarcinoma

In this example, a total of 158 tumors were subjected to MLH1 mutation analysis by direct sequencing of PCR products for examining the mutation status of MLH1 in a larger set of EGFR L858R-positive lung adenocarcinomas.
[PCR and Sanger Sequencing]

Exon 12 of the MLH1 gene was amplified from genomic DNA by PCR using a forward primer (SEQ ID NO: 05: 5'-CAGACTTTGCTACCAGGACTTGC-3') and a reverse primer (SEQ ID NO: 06: 5'-CTGCCTAGCCCTGC-CACTAG-3'). PCR products were sequenced using the Sanger method. DNA sequences were analyzed by the Mutation Surveyor software (SoftGenetics, State College, Pa.).
[Results]

Figure 2:
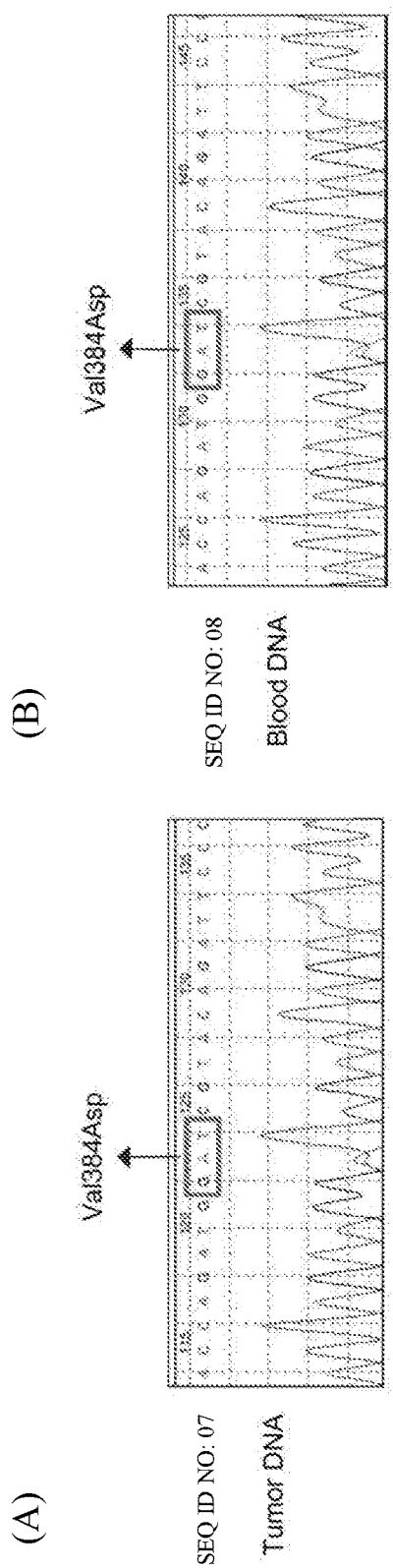
FIG. 2 shows the results of Sanger sequencing in Example 3, which indicates the mutation of V384D. (A) (SEQ ID NO: 7) DNA from tumor sample. (B) (SEQ ID NO: 8) DNA from blood sample.

Fourteen of the 158 tumors (8.9%) had a heterozygous T→A change at nucleotide 1151 (FIGS. 2A and 2B) which results in the same V384D substitution in MLH1 as discovered in NGS screening. We were able to analyze genomic DNA from blood specimens of 4 patients and non-tumor tissue specimens from 1 patient, and all of these samples were tested positive for MLH1 V384D (FIG. 2B). Clinical characteristics of patients with or without MLH1 V384D were analyzed (Table 1), and no statistically significant demographic differences between the two groups were noted. We also performed sequencing analysis of MLH1 exon 12 in 51 EGFR-wildtype lung adenocarcinomas and found a comparable incidence (4/51, 7.8%) of the MLH1 V384D allele.

TABLE 1

Patient characteristics (n = 158)

| | MLH1 codon 384 | | |
|---|---|---|---|
| | V/V | V/D | P value |
| Total case number | 144 | 14 | |
| Gender | | | 0.577 |
| Male | 50 | 5 | |
| Female | 94 | 9 | |
| Age | | | 0.240 |
| Median | 65 | 60 | |
| (Range) | (38-94) | (43-78) | |
| Smoking | | | 0.096 |
| Never | 111 | 8 | |
| Ever | 33 | 6 | |
| Stage | | | 0.119 |
| IIIB | 5 | 2 | |
| IV | 139 | 12 | |
| Number of prior chemotherapy | | | 0.661 |
| 0 | 116 | 12 | |
| 1 | 24 | 2 | |
| 2 | 4 | 0 | |
| EGFR mutation | | | 0.756 |
| L858R | 141 | 14 | |
| L858R, complex | 3 | 0 | |
| EGFR-TKI | | | 0.897 |
| Gefitinib | 120 | 12 | |
| Erlotinib | 23 | 2 | |
| Afatinib | 1 | 0 | |

Example 4: Tumor Response to EGFR-TKI

Figure 3:
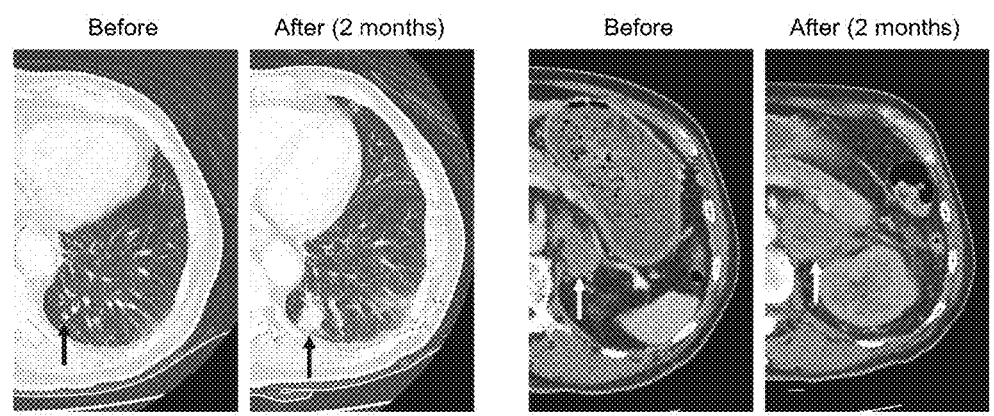
FIG. 3 shows images of chest CT scans of lung (black arrow) and adrenal gland (white arrow) metastases of a lung cancer patient with MLH1 V384D mutation before and after Erlotinib (Tarceva®) treatment.

In this example, a patient with MLH1 V384D mutation was monitored for two months after being treated with Erlotinib (Tarceva®) (a commercial EGFR-TKI drug). The chest CT scans (FIG. 3) of the patient showed that lung (black arrow) and adrenal gland (white arrow) metastasis remained persistent growth after treatment. The observation indicates the poor efficacy of EGFR-TKI therapy in patients with MLH1 V384D mutation. The response rate was calculated by the following equation:

$$\frac{\text{Number of patients having tumor size decrease} \geq 30\%}{\text{Total number of the patients be monitored}} \times 100\%$$

Figure 4A:
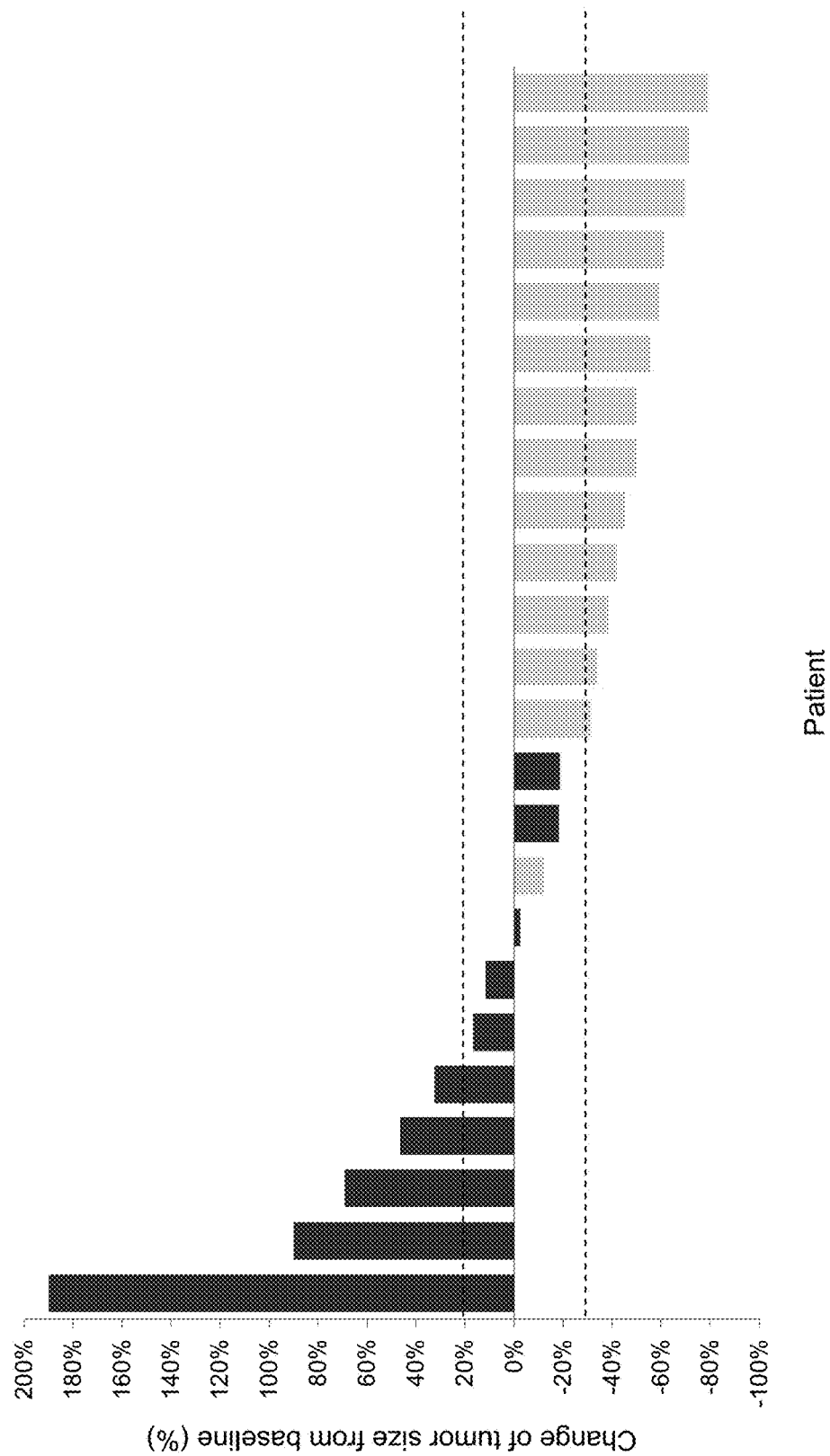
FIGS. 4A and 4B show the waterfall plots of tumor size percentage change from baseline in measureable tumors. (A) data from the 29 patients in Example 2; wherein 24 of them were monitored. (B) data from the 158 patients in Example 3; wherein 155 of them were monitored.

We evaluated individual tumor responses to EGFR-TKIs in patients whose tumors were of measurable sizes. 24 of the NGS-screened 29 patients (in above Examples 1 & 2; wherein 10 of them are with MLH1 V384D mutation and 14 of them are without) were monitored, and the tumor responses and PFS clustered correspondingly (FIG. 4A); 5 of 10 (50%) patients with short PFS had progressive disease (increase of tumor size ≥20%) whilst on EGFR-TKI treatment; and 5 of 10 (50%) patients with short PFS had stable disease (increase of tumor size ≤20% to decrease of tumor size ≤30%). 13 of 14 (92.9%) patients with long PFS had a partial response to EGFR-TKIs (decrease of tumor size ≥30%). The response rate for patient with MLH1 V384D mutation is 0%.

Figure 4B:
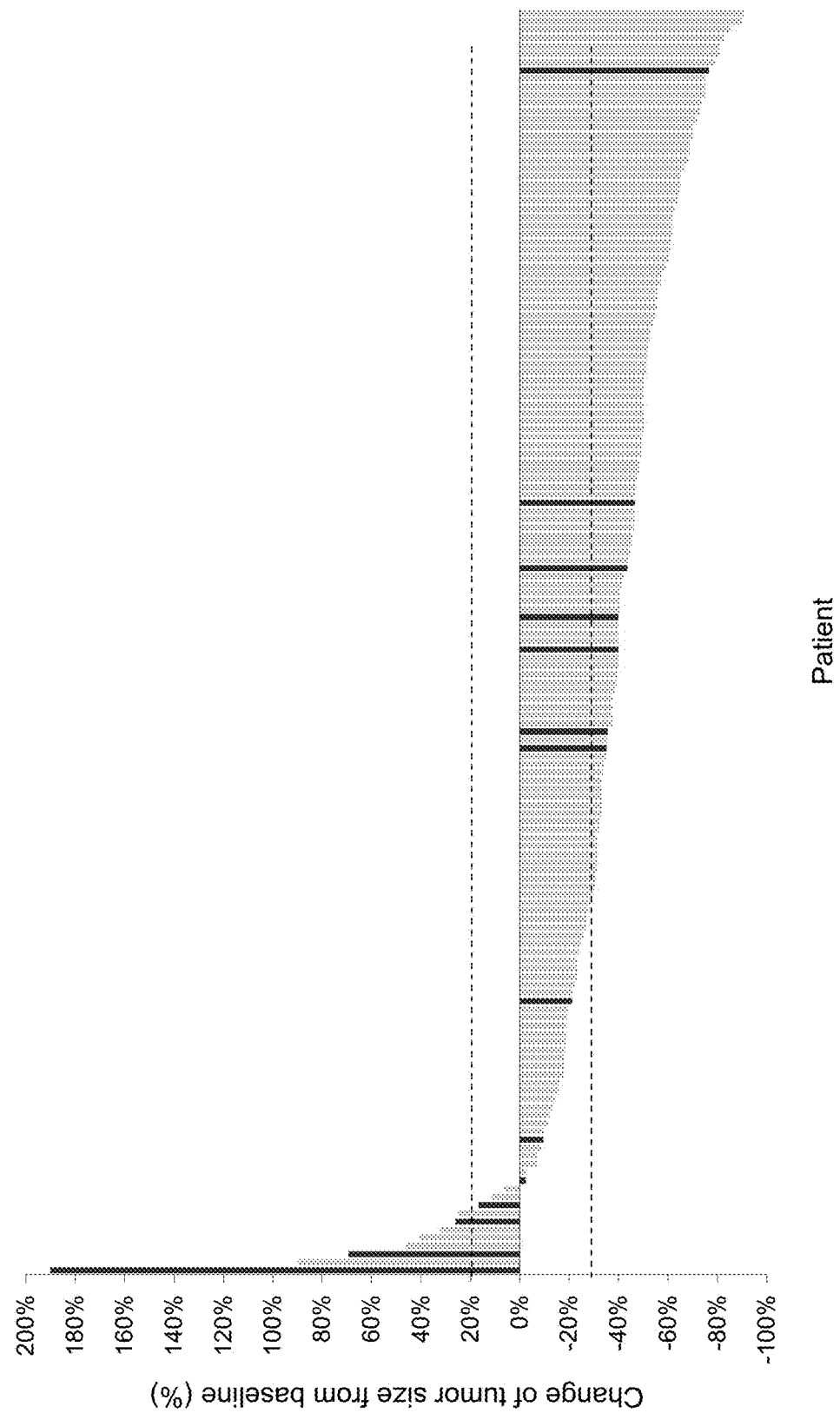

A same examination was also conducted in the 158 patients examined for MLH1 mutations by PCR and Sanger sequencing in the above Example 3. Among the 158 patients, 155 had measurable tumors and their responses to EGFR-TKIs were monitored (FIG. 4B). The overall response rate was 69.7%; 108, 39 and 8 patients achieved partial response, stable disease and progressive disease, respectively. The response rates for tumors with and without MLH1 V384D mutation were 50% and 71.6%, respectively (P=0.088). MLH1 V384D-positive tumors had a smaller size reduction in response to EGFR-TKI treatment than that in tumors without the allele (median size change −28.2% vs. −40.5%, P=0.015, Mann-Whitney U test). The MLH1 V384D allele was over-represented in patients with EGFR-TKI resistance. Only 11 of 155 (7.1%) EGFR L858R-positive tumors showed disease progression under EGFR-TKI treatment, and 4 of these 11 (36.4%) had MLH1 V384D. Among the 144 tumors either showing a partial response or being stable on treatment, only 10 (6.9%) were MLH1 V384D-positive.

Example 5: Survival Analysis

In this example, the 158 patients in the above Example 3 were monitored to record their progression-free survival (PFS). At the time of analysis, with a median follow-up of 47.4 months, 51 patients remained in use of an EGFR-TKI treatment and 107 patients (67.7%) had experienced PFS. The overall median PFS was 10.5 months (95% CI, 8.1 to 12.8 months).

Figure 5:
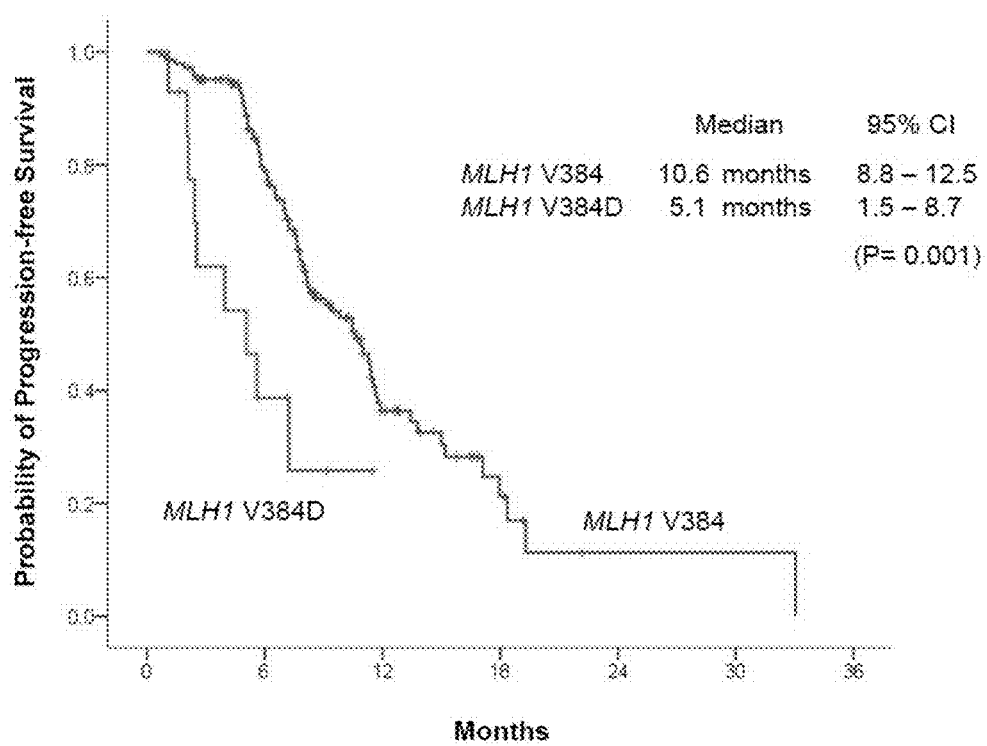
FIG. 5 shows the progression-free survival of the 158 patients of Example 3 after EGFR-TKI treatment.

Patients with the MLH1 V384D mutation had a significant shorter PFS (median, 5.1 months; 95% CI, 1.5 to 8.7 months) than that of those without (median, 10.6 months; 95% CI, 8.8 to 12.5 months) (P=0.001) (FIG. 5, Table 2). Gender (male vs. female, P=0.031) and the number of prior chemotherapy (0 vs. ≥1, P=0.002) were also predictor variables for PFS. In the multivariate analysis using the Cox regression model, only the number of prior treatment (HR=2.3, 95% CI, 1.4 to 3.8; in favor of none; P=0.001) and the MLH1 mutation status (HR=3.5, 95% CI, 1.7 to 7.2; in favor of no V384D mutation; P=0.001) were independent predictors for PFS.

TABLE 2

Numbers of progression-free subjects after EGFR-TKI treatment

| | Months | | | | | | |
|---|---|---|---|---|---|---|---|
| | 0 | 6 | 12 | 18 | 24 | 30 | 36 |
| MLH1 V384 | 144 | 94 | 24 | 6 | 2 | 1 | 0 |
| MLH1 V384D | 14 | 4 | 0 | 0 | 0 | 0 | 0 |

What is claimed is:

1. A method for treating a subject with lung cancer with a non-EGFR-TKI treatment, said method comprising:
   (A) obtaining a sample from said subject;
   (B) detecting a V384D alteration in a MLH1 protein-encoding nucleic acid of said sample by analyzing a sequence of MLH1 DNA, a sequence of MLH1 mRNA, and/or a cDNA sequence from said MLH1 mRNA of said sample; and
   (C) administering a non-EGFR-TKI treatment to said subject.

2. The method of claim 1, wherein said alteration corresponds with a T1349A mutation of said MLH1 mRNA.

3. The method of claim 1, wherein said alteration corresponds with a T1151A mutation of said cDNA.

4. The method of claim 1, wherein said analyzing is performed by polymerase chain reaction, Southern blot or a combination thereof.

5. The method of claim 1, wherein said analyzing is performed by using a primer set, a probe, or a combination thereof.

6. The method of claim 5, wherein said primer set comprises SEQ ID NO: 05 and SEQ ID NO: 06.

* * * * *